United States Patent
Edwards, Jr. et al.

(10) Patent No.: US 7,067,138 B1
(45) Date of Patent: Jun. 27, 2006

(54) PHARMACEUTICAL COMPOSITIONS AND METHODS TO VACCINATE AGAINST DISSEMINATED CANDIDIASIS

(75) Inventors: John E. Edwards, Jr., Palos Verdes, CA (US); Scott G. Filler, Rancho Palos Verdes, CA (US); Donald C. Sheppard, Montreal (CA); Ashraf S. Ibrahim, La Mirada, CA (US); Yue Fu, Torrance, CA (US); Bradley J. Spellberg, Ranchos Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 27 days.

(21) Appl. No.: 09/715,876

(22) Filed: Nov. 18, 2000

Related U.S. Application Data

(60) Provisional application No. 60/166,663, filed on Nov. 19, 1999.

(51) Int. Cl.
- *A61K 39/00* (2006.01)
- *A61K 38/00* (2006.01)
- *C07K 1/00* (2006.01)
- *C07K 2/00* (2006.01)

(52) U.S. Cl. .............. 424/274.1; 424/184.1; 424/185.1; 530/350; 530/300; 530/824; 530/806; 514/2

(58) Field of Classification Search .......... 530/350, 530/300, 824, 806; 424/184.1, 185.1, 274.1, 424/93.51, 192.1; 514/2
See application file for complete search history.

(56) References Cited

U.S. PATENT DOCUMENTS

| | | | | |
|---|---|---|---|---|
| 5,668,263 A | * | 9/1997 | Hoyer et al. | 536/23.1 |
| 5,817,466 A | * | 10/1998 | Hoyer et al. | 435/6 |
| 6,747,137 B1 | * | 6/2004 | Weinstock et al. | 536/23.1 |

OTHER PUBLICATIONS

Hoyer et al. J. Bacteriol. 180 (20): 5334-5343, Oct. 1998.*
Harlow et al. In: Antibodies: A Laboratory Manual. Cold Spring Harbor Laboratory, Chapter 5, p. 76, 1988.*
Kraus et al. J. Immunol. 139: 3084-3090, 1987.*
Barki, M., Y. Koltin, M. Yanko, A. Tamarkin, and M. Rosenberg. 1993. Isolation of a *Candida albicans* DNA sequence conferring adhesion and aggregation on *Saccharomyces cerevisiae*. J. Bacteriol. 175:5683-5689.
Bendel, C. M. and M. K. Hostetter. 1993. Distinct Mechanisms of Epithelial Adhesion for *Candida albicans* and *Candida tropicalis*. J. Clin. Invest. 92:1840-1849.
Caesar-TonThat, T. C. and J. E. Cutler. 1997. A monoclonal antibody to *Candida albicans* enhances mouse neutrophil candidacidal activity. Infect. Immun. 65:5354-5357.
Castaldo, P., R. J. Stratta, R. P. Wood, and et al. 1991. Clinical spectrum of fungal infections after orthotopic liver transplantation. Arch. Surg. 126:149-156.
Cutler, J. E., D. L. Brawner, K. C. Hazen, and M. A. Jutila. 1990. Characteristics of *Candida albicans* adherence to mouse tissues. Infect. Immun. 58:1902-1908.
De, Bernardis, F., M. Boccanera, D. Adriani, E. Spreghini, G. Santoni, and A. Cassone. 1997. Protective role of antimannan and anti-aspartyl proteinase antibodies in an experimental model of *Candida albicans* vaginitis in rats. Infect. Immun. 65:3399-3405.
Dromer, F., J. Charreire, A. Contrepois, C. Carbon, and P. Yeni. 1987. Protection, of mice against experimental cryptococcosis by anti-cryptococcus neoformans monoclonal antibody. Infect. Inimun. 55:749-752.

(Continued)

*Primary Examiner*—S. Devi
(74) *Attorney, Agent, or Firm*—Orrick Herrington & Sutcliffe LLP

(57) ABSTRACT

A *Candida albicans* bloodstream infections cause significant morbidity and mortality in hospitalized patients. Filament formation and adherence to host cells are critical virulence factors of *C. albicans*. Multiple filamentation regulatory pathways have been discovered, however the downstream effectors of these regulatory pathways remain unknown. The cell surface protein, Als1p, is a downstream effector of the filamentation regulatory pathway and is regulated by Efg1p. Als1p mediates adherence to endothelial cells in vitro and is required for virulence. The blocking of adherence by the organism is described resulting from the use of a composition and method disclosed herein. Specifically, a pharmaceutical composition comprised of a gene product from the ALS1 gene family is administered as a vaccine to generate an immune response capable of blocking adherence of the organism.

4 Claims, 14 Drawing Sheets

OTHER PUBLICATIONS

Ekenna, O., R. J. Sherertz, and H. Bingham. 1993. Natural history of bloodstream infections in a burn patient population: the importance of candidemia. Am. J. Infect. Control. 21:189-195.

Fisher-Hoch, S. P. and L. Hutwagner. 1995. Opportunistic candidiasis: an epidemic of the 1980's. Clin. Infect. Dis. 21:897-904.

Fonzi, W. A. and M. Y. Invin. 1993. Isogenic strain construction and gene mapping in Candida albicans. Genetics 134:717-728.

Fu, Y., S. G. Filler, B. J. Spellberg, W. Fonzi, A. S. Ibrahim, T. Kanbe, M. A. Ghannoum, and J. E. J. Edwards. 1998. Cloning and characterization of CAD I/AAF1, a gene from Candida albicans that induces adherence to endothelial cells after expression in Saccharomyces cerevisiae. Infect. Immun. 1998, 66:2078-2084.

Fu, Y., A. S. Ibrahim, W. Fonzi, X. Zhou, C. F. Ramos, and M. A. Ghannourn. 1997. Cloning and characterization of a gene (LIPI) which encodes a lipase from the pathogenic yeast Candida albicans. Microbiology. 1997 143:331-340.

Fu, Y., G. Rieg, W. A. Forizi, P. H. Belanger, J. E. J. Edwards, and S. G. Filler. 1998. Expression of the Candida albicans gene ALSI in Saccharomyces cerevisiae induces adherence to endothelial and epithelical cells. Infect. Immun. 66:1783-1786.

Gale, C., D. Finkel, N. Tao, 1%1. Meinke, M. McClellan, J. Olson, K. Kendrick, and M. Hostetter. 1996. Cloning and expression of a gene encoding an integrin-like protein in Candida albicans. Proc. Nad. Acad. Sci. U. S. A. 93:357-361.

Gale, C. A., C. M. Bendel, M. McClellan, M. Hauser, J. M. Becker, J. Berman, and K. Hostetter. 1998. Linkage of adhesion, filamentous growth, and virulence in Candida albicans to a single gene, INT1. Sci. 279:1355-1358.

Gaur, N. K. and S. A. Klotz. 1997. Expression, cloning, and characterization of a Candid albicans gene, AL41, that confers adherence properties upon Saccharomyces cerevisiae for extracellular matrix proteins. Infect. Immun. 65:5289-5294.

Gietz, R. D., R. H. Schiestl, A. R. Willems, and R. A. Woods. 1995. Studies on the transformation of intact yeast cells by the LiAc/SS-DNA/PEG procedure. Yeast. 11 :355-360.

Gustafson, K. S., G. M. Vercellotti, C. M. Bendel, and M. K. Hostetter. 1991. Molecular mimicry in Candida albicans. Role of an integrin analogue in adhesion of the yeast to human endothelium. J. Clin. Invest. 87:1896-1902.

Han, Y. and J. E. Cutler. 1995. Antibody response that protects against disseminated candidiasis. Infect. Immun. 63:2714-2719.

Hasenclever, H. F. and W. O. Mitchell. 1960. Antigenic relationships of Torulopsis glabrata and seven species of the genus Can&da. J. Bacteriol. 79:677-681.

Hoyer, L.L. 1997. The ALS gene family of Candida albicans. International Society for Human and Animal Mycology Salsimorge, Italy:(Abstract).

Hoyer, L. L., S. Scherer, A. R. Shatzman, and G. P. Livi. 1995. Candida albicans ALSI: domains related to a Saccharonzyces cerevisiae sexual agglutinin separated by a repeating motif. Mol. Microbiol. 1995, 15:39-54.

Jaffe, E. A., R. L. Nachman, C. G. Becker, and C. R. Ninick. 1973. Culture of human endothelial cells derived. from umbilical veins: identification by morphologic, and immunologic criteria. J. Clin. Invest. 52:2745-2756.

Jarvis, W.R. and H. and the National Nosocomial Infections Surveillance System. 1991. Predominant pathogens in hospital infection. 17th Internat'l Congress Chemoth (Abstract).

Jimenez-Lucho, V., V. Ginsburg, and H. C. Krivan. 1990. Cryptococcus neoformans, Candida albicans, and other fungi bind specifically to the glycosphingolipid lactosylceramide (Ga1P1-4G1cP1-1Cer), a possible adhesion receptor for yeasts. Infect. Immun. 58:2085-2090.

Kim, J. A.9 M. C. Territo, E. Wayner, T. M. Carlos, F. Parhami, C. W. Smith, M. E. Haberland, A. M. Fogellman, and J. A. Berliner. 1994. Partial characterization of leukocyte binding molecules on endothelial cells induced by minimally oxidized LDL. Arterioscler. Thromb. 14:427-433.

Klein, B. S. 1997. Role of cell surface molecules of Blastomyces dernzatitidis in the pathogenesis and inimunobiology of blastomycosis. Semin. Respir. Infect. 12:198-205.

Klotz, S. A., R. L. Smith, and B. W. Stewart. 1992. Effect of an arginine-glycineaspartic acid-containing peptide on hematogenous candidal infections in rabbits. Antimicrob. Agents Chemother. 36:132-136.

Lipke, P. N., D. Wojciechowicz, and J. Kurjan. 1989. AG alpha I is the structural gene for the Saccharomyces cerevisiae alpha-agglutinin, a cell surface glycoprotein involved in cell-cell interactions during mating. Mol. Cell Biol. 9:3155-3165.

Lotter, H., T. Zhang, K. B. Seydel, S. L. J. Stanley, and E. Tannich. 1997. Indentification of an epitope on the Entamoeba histolytica 170-kD lectin conferring antibody-mediated protection against invasive amebiasis. J. Exp. Med. 185:1793-1801.

Manjarrez-Hernandez, A., S. Gavilanes-Parra, M. E. Chavez-Berrocal, J. MolinalLopez, and A. Cravioto. 1997. Binding of diarrheagenic Escherichia coli to 32- to 33kilodalton human intestinal brush border proteins. Infect. Immun. 65:4494-4501.

Mayer, C. L., R. D. Diamond, and J. E. Edwards, Jr. 1990. Recognition of binding sites on Candida albicans by monoclonal antibodies to human leukocyte antigens. Infect. Immun. 58:3765-3769.

Mayer, C. L., S. G. Filler, and J. E. Edwards, Jr. 1992. Candida albicans adherence to endothelial cells. Microvasc. Res. 43:218-226.

Mukherjee, J., M. D. Scharff, and A. Casadevall. 1992. Protective murine monoclonal antibodies to Cryptococcus neoformas. Infect. Immun. 60:4534-4541.

Palaszynski, S., J. Pinkner, S. Leath, P. Barren, C. G. Auguste, J. Burlein, S. J. Hultgren, and S. Langermann. 1998. Systemic immunization with conserved pilusassociated adhesins protects against mucosal infections. Dev. Biol. Stand 92:117-122.

Panaretou, B. and P. Piper. 1996. Isolation of yeast plasma membranes. p. 117-121. In I.H. Evans. (ed.), Yeast Protocols. Methods in Cell and Molecular Biology. Human Press, Totowa, New Jersey.

Patti, J. M., B. L. Allen, M. J. McGavin, and M. Hook. 1994. MSCRAMM-mediated adherence of microorganisms to host tissues. Annu. Rev. Microbiol. 48:585-617.

Perraut Jr LE. 198 1. Successful treatment of Candida albicans endophthalmitis with intravitreal amphotericin B. Arch Ophthalmol 99:1565-1565.

Pfaller, M. A., R. N. Jones, S. A. Messer, M. B. Edmond, and R. P. Wenzel. 1998. National surveillance of nosocomial blood stream infection due to species of Candida other than Candida albicans: frequency of occurrence and antifungal susceptibility in the SCOPE Program. SCOPE Participant Group. Surveillance and Control of Pathogens of Epidemiologic. Diagn. Microbiol. Infect. Dis. 30:121-129.

Polak, A. 1987. Combination therapy of experimental candidiasis, cryptococcosis, aspergillosis and wangiellosis in mice, Chernother. 33:381-395.

Prasadarao, N. V., C. A. Wass, and K. S. Kim. 1997. Identification and characterization of S fimbria-binding sialoglycoproteins on brain microvascular endothelial cells. Infect. Immun. 65:2852-2860.

Rieg, G., Y. Fu, A. Ibrahim. X. Zhou, S. G. Filler, and J. E. Edwards Jr. 1998. Heterogeneity among single/double knock-out mutants of CAD11AAF1 in *Candida albicans*. (Submitted). Infect. Immun.

Rostrosen, D., J. E. Edwards, Jr., T. R. Gibson, J. C. Moore, and A. H. Cohen. 1985. Adherence of *Candida* to cultured vascular endothelial cells: mechanisms of attachment and endothelial cell penetration. J. Infect. Dis. 152:1264-1274.

Sanford, J. E., D. M. Lupan, A. M. Schlageter, and T. R. Kozel. 1990. Passive immunization against *Cryptococcus neoformans* with an isotype-switch family of monoclonal antibodies reactive with cryptococcal polysaccharide. Infect. Inunun. 58:1919-1923.

Sanger, F. and A. R. Coulson. 1975. A rapid method for determining sequences in DNA by primed synthesis with DNA polymerase. J. Mol. Biol. 94:441-448.

Saporito-Irwin, S. M., C. E. Birse, P. S. Sypherd, and W. A. Fonzi. 1995. *PHR1*, a pH-regulated gene of *Candida albicans*, is required for morphogenesis. Mol. Cell. Biol. 15:601-613.

Schnaar, R. L. 1994. Isolation of glycosphingolipids. Methods Enzymol. 230:348-370.

Sheth, H. B., L. M. Glasier, -N. W. Ellert, P. Cachia, W. Kohn, K. K. Lee, W. Paranchych, R. S. Hodges, and R. T. Irvin. 1995. Development of an anti-adhesive vaccine for *Pseudomonas aeruginosa* targeting the C-terminal region of the pilin structural protein. Biomed. Pept. Proteins Nucleic. Acids. 1:141-148.

Wenzel, R. P. and M. A. Pfaller. 1991. Candida species: emerging hospital bloodstream pathogens [editorial]. Infect. Control. Hosp. Epiderniol. 12:523-524.

Wey, S. B., M. Mori, M. A. Pfaller, R. F. Woolson, and R. P. Wenzel. 1988. Hospital-acquired candidernia. The attributable mortality and excess length of stay. Arch Intern Med 148:2642-2645.

Wojciechowicz, D., C. F. Lu, J. Kurjan, and P. N. Lipke. 1993. Cell surfaceanchorage and ligand-binding domains of the *Saccharomyces cerevisiae* cell adhesion protein alpha-agglutinin, a member of the immunoglobulin superfamily. Mol. Cell Biol. 13:2554-2563.

Yan, S., R. G. Rodrigues, and D. D. Roberts. 1998. Hemoglobin-induced binding of *Candida albicans* to the cell-binding domain of fibronectin is independent of the Arg-Gly-Asp sequence. Infect. Inunun. 66:1904-1909.

* cited by examiner

FIG. 7

```
1     ATGCTTCAACAATTTACATTGTTATTCCTATATTTGTCAATTGCAAGTGCAAAGACAATC
1      M  L  Q  Q  F  T  L  L  F  L  Y  L  S  I  A  S  A  K  T  I

61    ACTGGTGTTTTTGATAGTTTTAATTCATTAACTTGGTCCAATGCTGCTAATTATGCTTTC
21     T  G  V  F  D  S  F  N  S  L  T  W  S  N  A  A  N  Y  A  F

121   AAAGGGCCAGGATACCCAACTTGGAATGCTGTTTTGGGTTGGTCCTTAGATGGTACCAGT
41     K  G  P  G  Y  P  T  W  N  A  V  L  G  W  S  L  D  G  T  S

181   GCCAATCCAGGGGATACATTCACATTGAATATGCCATGTGTGTTTAAATATACTACTTCA
61     A  N  P  G  D  T  F  T  L  N  M  P  C  V  F  K  Y  T  T  S

241   CAAACATCTGTTGATTTAACTGCCGATGGTGTTAAATATGCTACTTGTCAATTTTATTCT
81     Q  T  S  V  D  L  T  A  D  G  V  K  Y  A  T  C  Q  F  Y  S

301   GGTGAAGAATTCACAACTTTTTCTACATTAACATGTACTGTGAACGACGCTTTGAAATCA
101    G  E  E  F  T  T  F  S  T  L  T  C  T  V  N  D  A  L  K  S

361   TCCATTAAGGCATTTGGTACAGTTACTTTACCAATTGCATTCAATGTTGGTGGAACAGGT
121    S  I  K  A  F  G  T  V  T  L  P  I  A  F  N  V  G  G  T  G

421   TCATCAACTGATTTGGAAGATTCTAAATGTTTTACTGCTGGTACCAATACAGTCACATTT
141    S  S  T  D  L  E  D  S  K  C  F  T  A  G  T  N  T  V  T  F

481   AATGATGGTGATAAAGATATCTCAATTGATGTTGAGTTTGAAAAGTCAACCGTTGATCCA
161    N  D  G  D  K  D  I  S  I  D  V  E  F  E  K  S  T  V  D  P

541   AGTGCATATTTGTATGCTTCCAGAGTTATGCCAAGTCTCAATAAGGTCACAACTCTTTTT
181    S  A  Y  L  Y  A  S  R  V  M  P  S  L  N  K  V  T  T  L  F

601   GTGGCACCACAATGTGAAAATGGTTACACATCTGGTACAATGGGGTTCTCCAGTAGTAAC
201    V  A  P  Q  C  E  N  G  Y  T  S  G  T  M  G  F  S  S  S  N

661   GGTGACGTTGCTATTGATTGCTCAAATATTCATATTGGTATCACAAAAGGATTAAATGAT
221    G  D  V  A  I  D  C  S  N  I  H  I  G  I  T  K  G  L  N  D

721   TGGAATTATCCGGTTTCATCTGAATCATTTAGTTACACTAAAACTTGTACATCTAATGGA
241    W  N  Y  P  V  S  S  E  S  F  S  Y  T  K  T  C  T  S  N  G

781   ATTCAGATTAAATATCAAAATGTACCTGCTGGTTATCGTCCATTTATTGATGCTTATATT
261    I  Q  I  K  Y  Q  N  V  P  A  G  Y  R  P  F  I  D  A  Y  I

841   TCTGCTACAGATGTTAACCAATATACTTTAGCATATACCAATGATTATACTTGTGCTGGC
281    S  A  T  D  V  N  Q  Y  T  L  A  Y  T  N  D  Y  T  C  A  G

901   AGTCGTCTGCAAAGTAAACCTTTCACTTTAAGATGGACTGGATACAAGAATAGTGATGCC
303    S  R  L  Q  S  K  P  F  T  L  R  W  T  G  Y  K  N  S  D  A

961   GGATCTAACGGTATTGTCATTGTTGCTACAACTAGAACAGTTACAGACAGTACCACTGCT
321    G  S  N  G  I  V  I  V  A  T  T  R  T  V  T  D  S  T  T  A

1021  GTCACTACTTTACCATTCAATCCAAGTGTTGATAAAACCAAAACAATCGAAATTTTGCAA
```

FIG. 7                                                          CONTINUED FROM FIGURE 7A

341         V  T  T  L  P  F  N  P  S  V  D  K  T  K  T  I  E  I  L  Q

1081    CCTATTCCAACCACTACCATCACAACTTCATATGTTGGTGTGACTACTTCCTATCTGACT
361       P  I  P  T  T  T  I  T  T  S  Y  V  G  V  T  T  S  Y  L  T

1141    AAGACTGCACCAATTGGTGAAACAGCTACTGTTATTGTTGATGTGCCATATCATACTACC
381       K  T  A  P  I  G  E  T  A  T  V  I  V  D  V  P  Y  H  T  T

1201    ACAACTGTTACCAGTGAATGGACAGGAACAATCACTACCACCACAACTCGTACCAATCCA
401       T  T  V  T  S  E  W  T  G  T  I  T  T  T  T  R  T  N  P

1261    ACTGATTCAATTGACACAGTGGTGGTACAAGTTCCACTGCCAAATCCAACTGTTAGTACT
421       T  D  S  I  D  T  V  V  V  Q  V  P  L  P  N  P  T  V  S  T

1321    ACTGAATATTGGTCTCAGTCCTTTGCTACAACCACTACAGTTACTGCTCCTCCAGGTGGT
441       T  E  Y  W  S  Q  S  F  A  T  T  T  T  V  T  A  P  P  G  G

1381    ACCGATACTGTGATTATCAGAGAGCCACCAAACCATACTGTCACTACTACTGAATATTGG
461       T  D  T  V  I  I  R  E  P  P  N  H  T  V  T  T  T  E  Y  W

1441    TCACAATCCTTTGCTACTACTACTACTGTTACTGCTCCTCCAGGTGGTACTGACTCAGTA
481       S  Q  S  F  A  T  T  T  T  V  T  A  P  P  G  G  T  D  S  V

1501    ATTATCAGAGAACCACCAAATCCAACTGTCACTACAACCGAGTATTGGTCTCAATCCTTT
501       I  I  R  E  P  P  N  P  T  V  T  T  T  E  Y  W  S  Q  S  F

1561    GCTACTACTACTACAGTTACTGCTCCTCCAGGTGGTACTGACTCAGTAATTATCAGAGAA
521       A  T  T  T  T  V  T  A  P  P  G  G  T  D  S  V  I  I  R  E

1621    CCTCCAAACCCAACTGTCACCACCACTGAATATTGGTCCCAATCTTACGCAACCACAACT
541       P  P  N  P  T  V  T  T  T  E  Y  W  S  Q  S  Y  A  T  T  T

1681    ACTGTGACTGCTCCTCCAGGAGGCACTGACTCAGTAATTATCAGAGAACCACCAAACCAC
561       T  V  T  A  P  P  G  G  T  D  S  V  I  I  R  E  P  P  N  H

1741    ACTGTCACTACTACTGAATACTGGTCACAATCATATGCCACCACTACCACTGTAACTGCA
581       T  V  T  T  T  E  Y  W  S  Q  S  Y  A  T  T  T  T  V  T  A

1801    CCACCAGGTGGTACTGACACTGTTATCATTAGAGAGCCACCAAACCACACTGTCACTACT
601       P  P  G  G  T  D  T  V  I  I  R  E  P  P  N  H  T  V  T  T

1861    ACTGAGTATTGGTCTCAATCGTTTGCTACTACCACAACTGTAACTGGTCCACCAAGTGGC
621       T  E  Y  W  S  Q  S  F  A  T  T  T  T  V  T  G  P  P  S  G

1921    ACTGATACTGTTATCATTAGGGAACCACCAAACCCAACTGTCACCACTACTGAATACTGG
641       T  D  T  V  I  I  R  E  P  P  N  P  T  V  T  T  T  E  Y  W

1981    TCTCAATCATATGCAACCACTACTACCATTACCGCTCCACCTGGTGAAACTGATACCGTT
661       S  Q  S  Y  A  T  T  T  T  I  T  A  P  P  G  E  T  D  T  V

2041    CTTATCAGAGAGCCACCAAACCATACTGTCACTACTACTGAATACTGGTCTCAATCATAT
681       L  I  R  E  P  P  N  H  T  V  T  T  T  E  Y  W  S  Q  S  Y

2101    GCTACAACCACCACTGTTACTGCACCACCTGGTGAAACCGATACCGTTCTTATCAGAGAG
701       A  T  T  T  T  V  T  A  P  P  G  E  T  D  T  V  L  I  R  E

2161    CCACCAAACCATACTGTCACTACTACTGAATACTGGTCTCAATCATATGCTACAACCACC

CONTINUED FROM FIGURE 7B

```
721    P  P  N  H  T  V  T  T  T  E  Y  W  S  Q  S  Y  A  T  T  T

2221   ACTGTTACTGCACCACCAGGTGGTACCGATACTGTTATCATTAGAGAGCCACCAAATCCA
741     T  V  T  A  P  P  G  G  T  D  T  V  I  I  R  E  P  P  N  P

2281   ACAGTTACTACTACTGAATATTGGTCACAATCATTTGCCACAACCACCACAGTTACTGCT
761     T  V  T  T  T  E  Y  W  S  Q  S  F  A  T  T  T  T  V  T  A

2341   CCTCCAGGTGGTACTGACACTGTGATTATCTATGAAAGCATGTCAAGTTCAAAGATTTCT
781     P  P  G  G  T  D  T  V  I  I  Y  E  S  M  S  S  S  K  I  S

2401   ACATCCTCCAATGATATAACCAGTATCATTCCATCATTTTCCCGTCCTCATTATGTCAAC
801     T  S  S  N  D  I  T  S  I  I  P  S  F  S  R  P  H  Y  V  N

2461   AGCACAACCTCCGATTTGTCAACATTTGAATCTTCATCCATGAATACTCCTACTTCTATC
821     S  T  T  S  D  L  S  T  F  E  S  S  S  M  N  T  P  T  S  I

2521   AGTAGTGATGGTATGTTGTTGTCTTCTACAACTTTGGTTACTGAATCAGAAACAACTACA
841     S  S  D  G  M  L  L  S  S  T  T  L  V  T  E  S  E  T  T

2581   GAACTGATTTGCAGTGATGGTAAAGAGTGTTCTAGATTGTCCAGTTCTTCTGGTATTGTC
861     E  L  I  C  S  D  G  K  E  C  S  R  L  S  S  S  S  G  I  V

2641   ACAAATCCAGATAGCAATGAATCCTCAATCGTAACTAGTACTGTTCCTACTGCAAGTACA
881     T  N  P  D  S  N  E  S  S  I  V  T  S  T  V  P  T  A  S  T

2701   ATGTCTGATTCACTTTCTTCAACTGATGGTATTAGTGCTACATCTTCTGATAATGTTTCA
901     M  S  D  S  L  S  S  T  D  G  I  S  A  T  S  S  D  N  V  S

2761   AAATCAGGAGTATCAGTTACAACCGAAACTTCTGTTACAACTATTCAAACTACTCCAAAC
921     K  S  G  V  S  V  T  T  E  T  S  V  T  T  I  Q  T  T  P  N

2821   CCATTATCATCTTCAGTGACATCATTGACTCAGTTGTCTTCAATTCCAAGTGTTTCAGAA
941     P  L  S  S  S  V  T  S  L  T  Q  L  S  S  I  P  S  V  S  E

2881   AGTGAAAGTAAAGTTACATTTACAAGCAATGGAGACAACCAAAGTGGTACTCATGATTCA
961     S  E  S  K  V  T  F  T  S  N  G  D  N  Q  S  G  T  H  D  S

2941   CAATCTACTTCCACTGAAATTGAAATTGTAACAACCAGTTCTACTAAAGTTTTACCACCT
981     Q  S  T  S  T  E  I  E  I  V  T  T  S  S  T  K  V  L  P  P

3001   GTCGTTTCTTCTAATACTGATTTGACTAGTGAACCAACAAATACCAGAGAACAACCAACT
1001    V  V  S  S  N  T  D  L  T  S  E  P  T  N  T  R  E  Q  P  T

3061   ACATTATCAACTACTTCAAACTCCATCACTGAAGATATCACCACATCTCAACCTACAGGT
1021    T  L  S  T  T  S  N  S  I  T  E  D  I  T  T  S  Q  P  T  G

3121   GATAATGGAGACAATACTTCATCAACCAATCCAGTTCCAACTGTGGCAACAAGTACTTTA
1041    D  N  G  D  N  T  S  S  T  N  P  V  P  T  V  A  T  S  T  L

3181   GCATCTGCAAGTGAAGAAGACAACAAAAGCGGTTCTCATGAATCAGCATCCACAAGTTTG
1061    A  S  A  S  E  E  D  N  K  S  G  S  H  E  S  A  S  T  S  L

3241   AAACCAAGTATGGGTGAAAATTCTGGATTAACTACTTCTACTGAAATTGAAGCTACAACA
1081    K  P  S  M  G  E  N  S  G  L  T  T  S  T  E  I  E  A  T  T

3301   ACCAGTCCTACAGAAGCTCCATCACCTGCTGTTTCTTCTGGTACTGATGTAACTACTGAA
```

CONTINUED FROM FIGURE 7C

```
1101    T  S  P  T  E  A  P  S  P  A  V  S  S  G  T  D  V  T  T  E

3361    CCAACTGATACTAGAGAACAACCTACTACATTATCAACTACTTCAAAAACAAACAGTGAA
1121     P  T  D  T  R  E  Q  P  T  T  L  S  T  T  S  K  T  N  S  E

3421    CTGGTTGCTACTACACAAGCTACTAATGAAAATGGTGGTAAATCTCCATCAACTGATTTA
1141     L  V  A  T  T  Q  A  T  N  E  N  G  G  K  S  P  S  T  D  L

3481    ACATCAAGCTTGACAACAGGCACCTCAGCATCTACAAGTGCTAATAGCGAACTTGTTACT
1161     T  S  S  L  T  T  G  T  S  A  S  T  S  A  N  S  E  L  V  T

3541    AGTGGATCTGTTACTGGTGGAGCTGTTGCCAGTGCTTCAAATGATCAATCACATTCTACT
1181     S  G  S  V  T  G  G  A  V  A  S  A  S  N  D  Q  S  H  S  T

3601    TCTGTTACCAACAGCAACAGCATTGTATCTAATACCCCACAAACTACATTGAGTCAACAA
1201     S  V  T  N  S  N  S  I  V  S  N  T  P  Q  T  T  L  S  Q  Q

3661    GTTACCTCATCCTCACCTTCAACCAACACATTCATTGCTTCTACATACGATGGCTCTGGT
1221     V  T  S  S  S  P  S  T  N  F  I  A  S  T  Y  D  G  S  G

3721    TCTATTATCCAACATTCTACTTGGTTGTACGGTTTGATCACATTATTGTCCTTGTTCATT
1241     S  I  I  Q  H  S  T  W  L  Y  G  L  I  T  L  L  S  L  F  I

3781    TAGTGA
1261     *  *
```

FIG. 7D

PHARMACEUTICAL COMPOSITIONS AND METHODS TO VACCINATE AGAINST DISSEMINATED CANDIDIASIS

RELATED INFORMATION

This application claims priority from Provisional Application Ser. No. 60/166,663 filed Nov. 19, 1999.

This invention was made with Government support under Public Health Service grants PO-1AI-37194, RO1AI-19990, and MO1 RR0425. The Government has certain rights in this invention.

FIELD OF INVENTION

This invention relates to *Candida albicans* surface adhesin proteins, to antibodies resulting from an immune response to vaccination, and to methods for the prevention and/or treatment of candidiasis.

BACKGROUND OF INVENTION

There has been a dramatic increase in the incidence of nosocomial infections caused by *Candida* species in recent years. The incidence of hematogenously disseminated candidal infections increased 11-fold from 1980 to 1989. This increasing incidence has continued into the 1990s. Infections by *Candida* species are now the fourth most common cause of nosocomial septicemia, are equal to that of *Escherichia coli*, and surpass the incidence caused by *Klebsiella* species. Furthermore, *Candida* species are the most common cause of deep-seated fungal infections in patients who have extensive burns. Up to 11% of individuals undergoing bone marrow transplantation and 13% of those having an orthotopic liver transplant will develop an invasive candidal infection.

*Candida albicans*, the major pathogen in this genus, can switch between two morphologies: the blastospore (budding yeast) and filamentous (hyphae and pseudohyphae) phases. *Candida* mutants that are defective in genes regulating filamentation are reported to have reduced virulence in animal models. This reduced virulence suggests that the ability to change from a blastospore to a filament is a key virulence factor of *C. albicans*. To date, no essential effectors of these filamentation pathways have been identified in *C. albicans*. See Caesar-TonThat, T. C. and J. E. Cutler, "*A monoclonal antibody to Candida albicans enhances mouse neutrophil candidacidal activity*," Infect. Immun. 65:5354–5357, 1997.

The identification of effectors in the regulatory pathways of the organism that contribute to virulence offers the opportunity for therapeutic intervention with methods or compositions that are superior to existing antifungal agents. The identification of cell surface proteins that effect a regulatory pathway involved in virulence is particularly promising because characterization of the protein enable immunotherapeutic techniques that are superior to existing antifungal agents when fighting a candidal infection.

The virulence of *Candida albicans* is regulated by several putative virulence factors of which adherence to host constituents and the ability to transform from yeast-to-hyphae are among the most critical in determining pathogenicity. While potent antifungal agents exist that are microbicidal for *Candida*, the attributable mortality of candidemia is approximately 38%, even with treatment with potent antifungal agents such as amphotericin B. Also, existing agents 20 such as amphotericin B tend to exhibit undesirable toxicity. Although additional antifungals may be developed that are less toxic than amphotericin B, it is unlikely that agents will be developed that are more potent. Therefore, either passive or active immunotherapy to treat or prevent disseminated candidiasis is a promising alternative to standard antifungal therapy.

SUMMARY OF INVENTION

The present invention utilizes the gene product of *C. albicans* agglutinin like sequence ALS1 as a vaccine to treat, prevent, or alleviate disseminated candidiasis. The invention takes advantage of the role of the ALS I gene product in the adherence of the *C. albicans* to endothelial and epithelial cells and the susceptibility of the ALS1-expressed surface protein for use as a vaccine to retard the pathogenesis of the organism.

Pursuant to this invention, the ALS1 gene encodes a surface adhesin that is selected as the target of an immunotherapeutic strategy against *Candida Albicans*. A demonstration that the expression product of the ALS1 gene, the ALS1p protein, has structural characteristics typical of surface proteins and is, in fact, expressed on the cell surface of *C. albicans* is a critical criterion for proteins that act as adhesins to host tissues. In this case, ALS1p has a signal peptide at the N-terminus, a glycosylphosphatidylinosine (GPI) anchorage sequence in the C-terminus, and a central region comprising repeats rich in threonine and serine. Also, the ALS 1 protein has many N-, and O-glycosylation sites, typical of proteins that are expressed on the cell surface. Indirect immunofluorescence using a monoclonal antibody directed against the N-terminus of Als1p revealed that Als1p is expressed during the log phase of blastospores. This expression of Als1p is increased during hyphal formation and is localized to the junction where the hyphal element extends from the blastospores as indicated by the diffused surface staining. Furthermore, this monoclonal antibody blocked the enhanced adherence of *C. albicans* overexpression mutant to endothelial cells, thereby establishing the principle for immunotherapy applications using Als1p.

Additional evidence that Als1p is a surface adhesin protein is based on data showing that antibodies that bind to the surface of *C. albicans* also bind to the surface of *S. cerevisiae* transformed with ALS1, but not with empty plasmid. The ALS1 protein also shares significant homology with the alpha-agglutinin of *S. cerevisiae*, which is expressed on the cell surface and mediates the binding of mating type alpha cells to mating type a cells. Moreover, expression of the ALS1 gene in *S. cerevisiae* increases the adherence of this organism to endothelial cells by approximately 100-fold. Because the ALS1 gene appears to encode a functional adhesin in *S. cerevisiae*, it is certain that it also encodes a functional adhesin in *C. albicans*. The ALS1 gene was originally isolated by Hoyer et al. without a known function. Hoyer, L. L., S. Scherer, A. R. Shatzman, and G. P. Livi. 1995. *Candida albicans* ALS1: domains related to a *Saccharomyces cerevisiae* sexual agglutinin separated by a repeating motif. Mol. Microbiol. 15:39–54. (See also U.S. Pat. Nos. 5,668,263 and 5,817,466.)

Thus, according to one aspect of the invention we provide an ALS1 surface adhesin protein, designated Als1p, or a fragment conjugate or analogue thereof, having useful properties when formulated in a pharmaceutical composition and administered as a vaccine. Als1p or functional analogues conjugates or derivatives thereof, is preferably obtained from *Candida albicans*. However, similar adhesin molecules or analogues or derivatives thereof may be of candidal origin and may be obtainable, for example, from strains belonging to the genera *Candida*, for example *Candida parapsilosis*, *Candida krusei*, and *Candida tropicalis*. A surface adhesin protein according to the invention may be obtained in purified form, and thus, according to a preferred embodiment of the invention a substantially pure ALS1 *Candida albicans* surface adhesin protein, or functional analogue conjugates or derivative thereof, is formulated as a vaccine to cause an immune response in a patent to block adhesion of the organism to the endothelial cells.

An analogue or derivative of the surface adhesion protein according to the invention may be identified and further characterized by the criteria described herein for the ALS1 gene and gene product. For example, a null mutant of the analogue or derivative would share markedly reduced adhesion to endothelial cells compared to controls. Similarly, over-expression of the analogue or derivative in an appropriate model would show an increased adherence to endothelial cells compared to controls and would be confirmed as a cell surface adhesin in accord with the criteria described above. Also, antisera to the analogue or derivative would cross-react with anti-ALS1 antibodies and would also exhibit increased survival times when administered in a mouse model of disseminated candidiasis as disclosed herein.

The present invention also provides an immunotherapeutic strategy against *Candida* infection at the level of binding to the vascular endothelial cells and through a downstream effector of the filamentation regulatory pathway. An immunotherapeutic strategy is uniquely advantageous in this context because: (i) the morbidity and mortality associated with hematogenously disseminated candidiasis remains unacceptably high, even with currently available antifungal therapy; (ii) a rising incidence of antifungal resistance is associated with the increasing use of antifungal agents, iii) the population of patients at risk for serious *Candida* infections is well-defined and very large, and includes postoperative patients, transplant patients, cancer patients and low birth weight infants; and iv) a high percentage of the patients who develop serious *Candida* infections are not neutropenic, and thus may respond to a vaccine. For these reasons, *Candida* is the most attractive fungal target for either passive or active immunotherapy.

Having determined the immunotherapeutic potential of Als1p according to this invention, this protein and conjugates analogues, or derivative molecules thereof may be used in treatment and/or prevention of candidal infections. Standard immunological techniques may be employed with the adhesion protein molecule, and its analogues, conjugates, or derivatives, to use the molecule as an immunogen in a pharmaceutically acceptable composition administered as a vaccine. For the purposes of this invention, "pharmaceutical" or "pharmaceutically acceptable" compositions are formulated by known techniques to be non-toxic and, when desired, used with carriers or additives that are approved for administration to humans in, for example, intravenous, intramuscular, intraperitoneal or sub-cutaneous injection. Such compositions may include buffers, salts or other solvents known to these skilled in the art to preserve the activity of the vaccine in solution.

With respect to the molecule used as the immunogen pursuant to the present invention, those of skill in the art will recognize that the Als1p molecule may be truncated or fragmented without losing the essential qualities as a vaccine. For example, Als1p may be truncated to yield an N-terminal fragment by truncation from the C-terminal end with preservation of the functional properties described above. Likewise, C-terminal fragments may be created by truncation from the N-terminal end with preservation of the functional properties described above. Other modifications in accord with the foregoing rationale may be made pursuant to this invention to create other Als1p analogs or derivatives, to achieve the benefits described herein with the native protein.

The goal of the immunotherapy provided by this invention to interfere with regulation of filamentation, to block adherence of the organism to host constituents, and to enhance clearance of the organism by immunoeffector cells. Since endothelial cells cover the majority of the vasculature, strategies to block the adherence of the organism to endothelial cells using antibodies are a preferred embodiment of the present invention and such adherence blocking strategies include active or passive immunotherapy directed against the candidal adhesin(s) disclosed herein. Thus, for example, any suitable host may be injected with protein and the serum collected to yield the desired anti-adhesin antibody after appropriate purification and/or concentration. Prior to injection, the adhesin protein may be formulated in a suitable vehicle, preferably a known immunostimulant such as a polysaccharide. Thus, according to a further aspect of the invention we provide a pharmaceutical composition comprising a candidal adhesin protein together with one or more pharmaceutically acceptable excipients in a formulation for use as a vaccine.

The method of the invention is ameliorating and/or preventing candidal infection by blocking the adherence of *C. albicans* to the endothelial cells of a host constituent. Thus, according to one aspect of the invention, a pharmaceutical composition comprising an ALS1 adhesin protein derivative, analogue, or conjugate is formulated as a vaccine in a pharmaceutical composition containing a biocompatible carrier for injection or infusion and is administered to a patient. Also, direct administration of antiserum raised against ALS1 protein may be used to block the adherence of *C. albicans* to a mammalian host constituent. Antiserum against adhesin protein can be obtained by known techniques, Kohler and Milstein, Nature 256: 495–499 (1975), and may be humanized to reduce antigenicity, see U.S. Pat. No. 5,693,762, or produced in transgenic mice leaving an unrearranged human immunoglobulin gene, see U.S. Pat. No. 5,877,397.

A still further use of the invention, for example, is using the ALS1 adhesin protein to develop vaccine strategies for the prevention and/or amelioration of candidal infections. Thus, according to one aspect of the invention, for example, standard immunology techniques may be employed to construct a multi-component vaccine strategy that may enhance and/or elicit immune response from a host constituent to bock adherence of *C. albicans*.

A still further use of the invention, for example, is developing DNA vaccine strategies. Thus, according to one aspect of the invention, for example, the ALS1 polynucleotide encoding Als1p on a fragment thereof is administered according to a protocol designed to yield an immune response to the gene product. See e.g., Felgner U.S. Pat. No. 5,703,055.

A still further use of the invention, for example, is developing combination vaccine strategies. Thus, according to one aspect of the invention, for example, anti-ALS antibodies may be used with antibodies in treating and/or preventing candidal infections. See U.S. Pat. No. 5,578,309.

DESCRIPTION OF THE FIGURES

FIG. 7 is the polynucleotide (SEQ ID NO.7) which encodes the polypeptide sequence of Als1p (SEQ ID NO.8).

DETAILED DESCRIPTION OF THE INVENTION

Figure 1A:
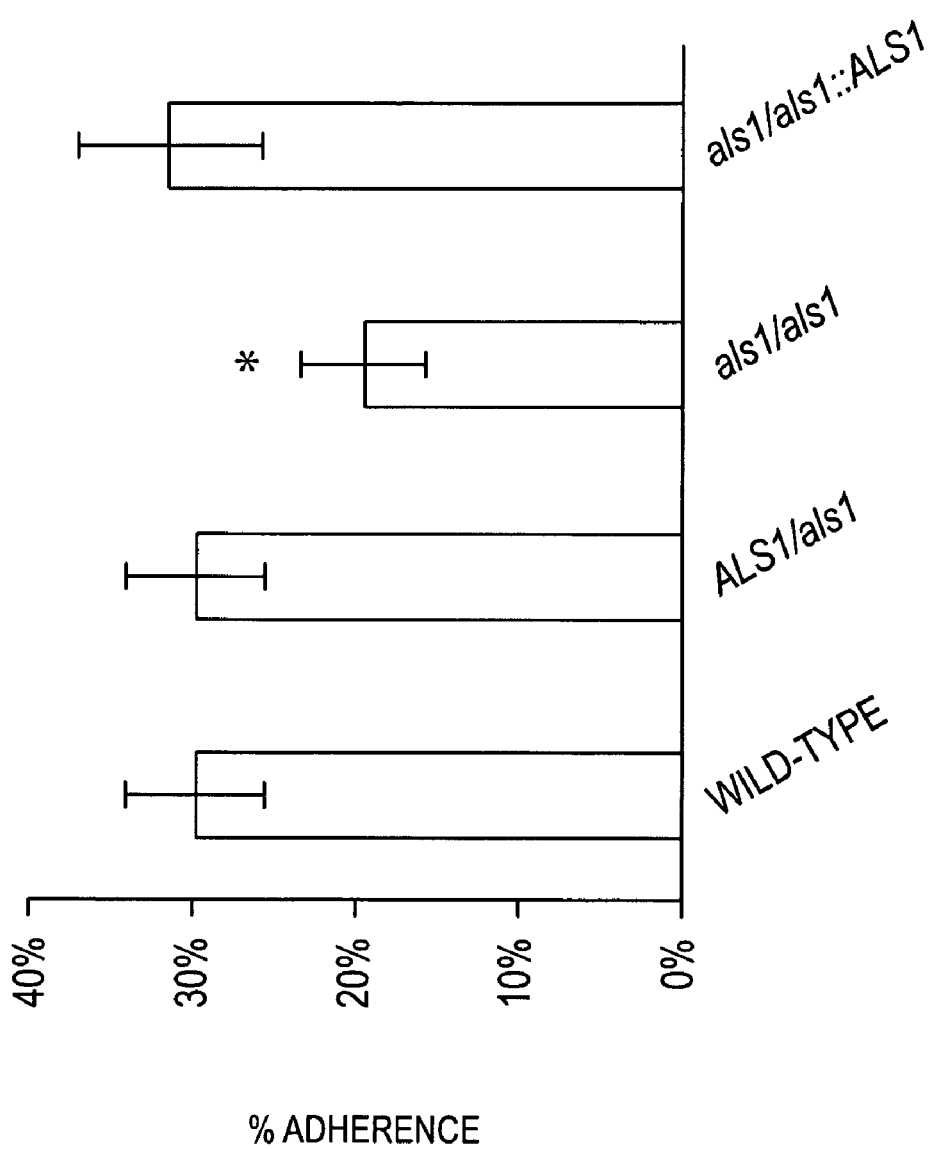
FIG. 1A, 1B show the mediation of Als1p adherence of *C. albicans* to human umbilical vein endothelial cells. Values represent the mean±SD of at least three independent experiments, each performed in triplicate. (A) Endothelial cell adherence of ALS1/als2, als1/als1 and ALS1-complemented mutants and wild-type CAI12 (30) (B) Endothelial cell adherence of $P_{ADH1}$-ALS1 mutant that overexpresses ALS1, compared to wild type *C. albicans*. Statistical treatment was obtained by Wilcoxon rank sum test and corrected for multiple comparisons with the Bonferroni correction. *P<0.001 for all comparisons.

The nature of the pathogenesis of *C. albicans* by adherence to endothelial cells is discussed in U.S. Pat. No. 5,578,309 which is specifically incorporated herein by reference in its entirety. For a description of the ALS1 gene and characteristics thereof, including the characterization of the gene product as an adhesin, see Fu, Y., S. G. Filler, B. J. Spellberg, W. Fonzi, A. S. Ibrahim, T. Kanbe, M. A. Ghannoum, and J. E. J. Edwards. 1998. Cloning and characterization of CAD I/AAF1, a gene from *Candida albicans* that induces adherence to endothelial cells after expression in Saccharonzyces cerevisiae. Infect. Immun. 66:2078–2084; Fu, Y., G. Rieg, W. A. Forizi, P. H. Belanger, J. E. J. Edwards, and S. G. Filler. 1998. Expression of the *Candida albicans* gene ALS1 in *Saccharomyces cerevisiae* induces adherence to endothelial and epithelial cells. Infect. Immun. 66:1783–1786; Hoyer, L. L. 1997. The ALS gene family of *Candida albicans*. International Society for Human and Animal Mycology Salsimorge, Italy: (Abstract); Hoyer, L. L., S. Scherer, A. R. Shatzman, and G. P. Livi. 1995. *Candida albicans* ALS1: domains related to a *Saccharonzyces cerevisiae* sexual agglutinin separated by a repeating motif. Mol. Microbiol. 15:39–54.

The following Examples illustrate the immunotherapeutic utility of the ALS1 adhesin as the basis for preventive measures or treatment of disseminated candidiasis. Example 1 describes the preparation of an ALS1 null mutant and a strain of *C. albicans* characterized by over-expression of ALS1 to confirm the mediation of adherence to endothelial cells. Example 2 describes the localization of Als1p and the implication of the efg filamentation regulatory pathway. Example 3 describes the purification of ALS1 adhesin protein. Example 4 describes the preparation of rabbit polyclonal antibodies raised against the ALS1 surface adhesin protein to be used to demonstrate the blocking of the surface adhesin protein. Example 5, describes the blocking of adherence in vivo, using polyclonal antibodies raised against the ALS1 surface adhesion protein as described herein according to the invention to protect against disseminated candidiasis in a mouse model.

EXAMPLE 1

Als1 Mediates Adherence of *C. albicans* to Endothelial Cells

The URA blaster technique was used to construct a null mutant of *C albicans* that lacks expression of the Als1p. The als1/als1 mutant was constructed in *C. albicans* strain CAI4 using a modification of the Ura-blaster methodology [W. A. Fonzi and M. Y. Irwin, *Genetics* 134, 717 (1993)] as follows: Two separate als1-hisG-IRA3-hisG-als1 constructs were utilized to disrupt the two different alleles of the gene. A 4.9 kb ALS1 coding sequence was generated with high fidelity PCR (Boehringer Mannheim, Indianapolis, Ind.) using the primers: 5'-CCGCTCGAGATGCTTCAACAATTTACAT-TGTTA-3' (SEQ ID NO.1) and 5'-CCGCTCGAGTCAC-TAAATGAACAAGGACAATA3' (SEQ BD NO.2). Next, the PCR fragment was cloned into pGEM-T vector (Promega, Madison, Wis.), thus obtaining pGEM-T-ALS1. The hisG-URA3-hisG construct was released from pMG-7 by digestion with Kpn1 and Hind3 and used to replace the portion of ALS1 released by Kpn1 and Hind3 digestion of pGEM-T-ALS1. The final als1-hisG-URA3-hisG-als1 construct was released from the plasmid by digestion with XhoI and used to disrupt the first allele of ALS1 by transformation of strain CAI-4.

A second als1-hisG-URA3-hisG-als1 construct was generated in two steps. First, a Bgl2-Hind3 hisG-URA3-hisG fragment of pMB7 was cloned into the BamH1–Hind3 sites of pUC19, thereby generating pYC2. PYC2 was then digested with Hind3, partially filled in with dATP and dGTP using T4 DNA polymerase, and then digested with Sma1 to produce a new hisG-URA3-hisG fragment. Second, to generate ALS1 complementary flanking regions, pGEM-T-ALS1 was digested with XbaI and then partially filled in with dCTP and dTTP. This fragment was digested with HpaI to delete the central portion of ALS1 and then ligated to the hisG-URA3-hisG fragment generating pYC3. This plasmid was then digested by XhoI to release a construct that was used to disrupt the second allele of the ALS1. Growth curves were done throughout the experiment to ensure that the generated mutations had no effect on growth rates. All integrations were confirmed by Southern blot analysis using a 0.9 kb ALS1 specific probe generated by digestion of pYF5 with XbaI and HindIII.

The null mutant was compared to *C. albicans* CAI-12 (a URA+ revertant strain) for its ability to adhere in vitro to human umbilical vein endothelial cells. For adherence studies, yeast cells from YPD (2% glucose, 2% peptone, and 1% yeast extract) overnight culture, were grown in RPMI with glutamine at 25° C. for 1 hour to induce Als1p expression. $3 \times 10^2$ organisms in Hanks balanced salt solution (HBSS) (Irvine Scientific, Irvine, Calif.) were added to each well of endothelial cells, after which the plate was incubated at 37° C. for 30 minutes. The inoculum size was confirmed by quantitative culturing in YPD agar. At the end of incubation period, the nonadherent organisms were aspirated and the endothelial cell monolayers were rinsed twice with HBSS in a standardized manner. The wells were over laid with YPD agar and the number of adherent organisms were determined by colony counting. Statistical treatment was obtained by Wilcoxon rank sum test and corrected for multiple comparisons with the Bonferroni correction. P<0.001.

Figure 1B:
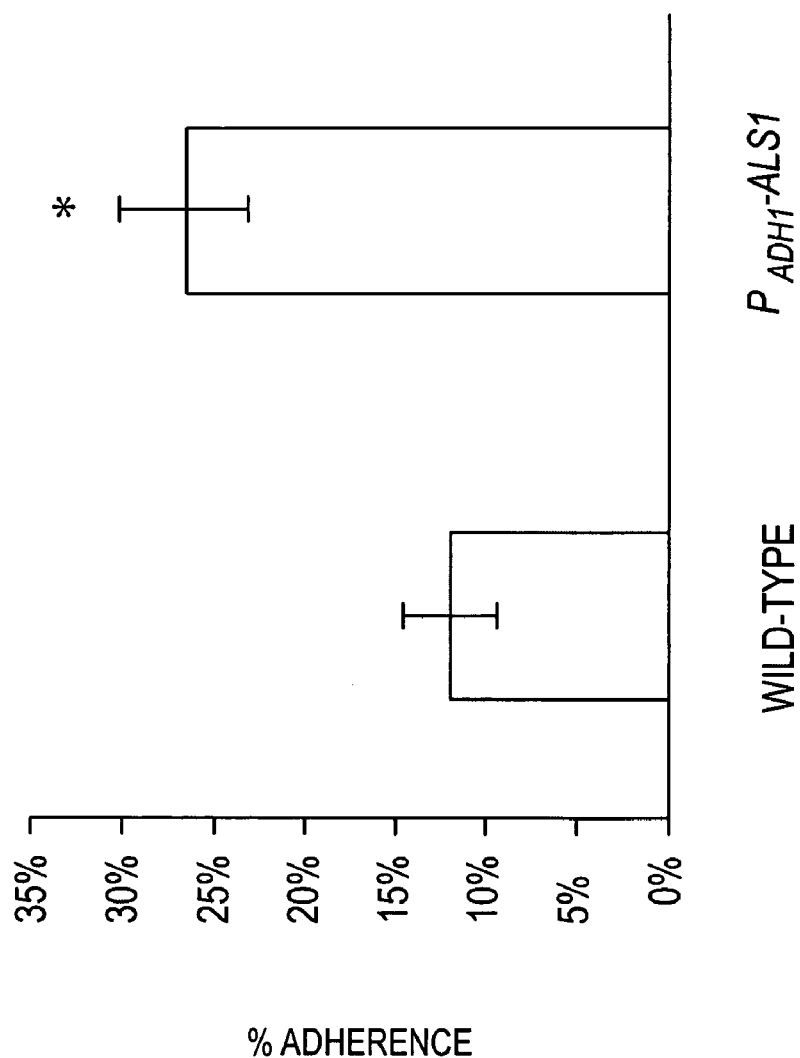

Referring to FIG. 1, a comparison of the ALS1/ALS1 and als1/als1 strain showed that the ALS1 null mutant was 35% less adherent to endothelial cells than *C. albicans* CAI-12. To reduce background adherence, the adherence of the wild-type strain grown under non-ALS1 expressing conditions was compared with a mutant autonomously expressing Als1p. This mutant was constructed by integrating a third copy of ALS1 under the control of the constitutive ADH1 promoter into the wild-type *C. albicans*. To achieve constitutive expression of the ALS1 in *C. albicans*, a blunt-ended PCR generated URA3 gene is ligated into a blunt-edged Bgl2 site of pOCUS-2 vector (Novagen, Madison, Wis.), yielding pOU-2. A 2.4 kb Not1-Stu1 fragment, which contained *C. albicans* alcohol dehydrogenase gene (ADH1) promoter and terminator (isolated from pLH-ADHpt, and kindly provided by A. Brown, Aberdeen, UK), was cloned into pOU-2 after digestion with Not1 and Stu1. The new plasmid, named pOAU-3 had only one Bgl2 site between the ADH1 promoter and terminator. ALS1 coding sequence flanked by BamH1 restriction enzyme sites was generated by high fidelity PCR using pYF-5 as a template and the following primers: 5'-CGGGATCCAGATGCTTCA-ACAATTTACATTG-3' (SEQ ID NO.3) and 5'-CGGGATC-CTCACTAAATGAACAAGGACAATA-3' (SEQ ID NO.4). This PCR fragment was digested with BamH1 and then cloned into the compatible Bg12 site of pOAU-3 to generate pAU-1. Finally, pAU-1 was linearized by XbaI prior to transforming *C. albicans* CAI-4. The site-directed integration was confirmed by Southern Blot analysis. Referring to FIG. 1B, overexpressing ALS1 in this $P_{ADH1}$-ALS1 strain resulted in a 76% increase in adherence to endothelial cells, compared to the wild-type *C. albicans*. In comparing endothelial cell adherence of the wild-type to that of the overexpressing mutant, yeast cells were grown overnight in YPD at 25° C. (non-inducing condition of Als1p). Als1p expression was not induced to reduce the background adherence of the wile-type, thus magnifying the role of Als1p in adherence through PADHI-ALS1 hybrid gene. The adherence assay was carried out as described above. Statistical treatment was obtained by Wilcoxon rank sum test and corrected for multiple comparisons with the Bonferroni correction. P<0.001.

A monoclonal anti-Als1p murine IgG antibody was raised against a purified and truncated N-terminus of Als1p (amino acid #17 to #432) expressed using CLONTECH™ [Clontech] YEXpress™ yeast expression system (Palo Alto, Calif.). The adherence blocking capability of these monoclonal anti-Als1p antibodies was assessed by incubating *C. albicans* cells with either anti-Als1 antibodies or mouse IgG (Sigma, St. Louis, Mo.) at a 1:50 dilution. After which the yeast cells were used in the adherence assay as described above. Statistical treatment was obtained by Wilcoxon rank sum test and corrected for multiple comparisons with the Bonferroni correction. P<0.001. The results revealed that the adherence of the $P_{ADH1}$-ALS1 strain was reduced from 26.8%±3.5% to 14.7%±5.3%. Thus, the effects of ALS1 deletion and overexpression demonstrate that Als1p mediates adherence of *C. albicans* to endothelial cells.

EXAMPLE 2

Localization of Als1p

Figure 2A:
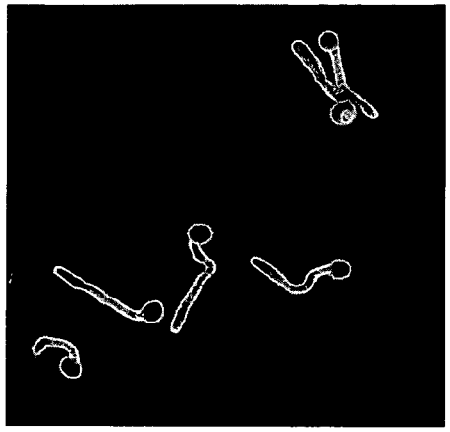
FIGS. 2A–D shows the cell surface localization of Als1p on filaments of *C. albicans* by indirect immunofluorescence. Filamentation of *C. albicans* was induced by incubating yeast cells in RPMI 1640 medium with glutamine for 1.5 hours at 37° C. Als1p was detected by incubating organisms first with anti-Als1p mouse mAb followed by FITC-labeled goat anti-mouse IgG. *C. albicans* cell surface was also stained with anti-*C. albicans* polyclonal Ab conjugated with Alexa 594 (Molecular Probes, Eugene, Oreg.). Areas with lighter staining represent Als1p localization. (A) *C. albicans* wild-type. (B) als1/als1 mutant strain. (C) als1/als1 complemented with wild type ALS1. (D) $P_{ADH1}$-ALS1 overexpression mutant.
Figure 2B:
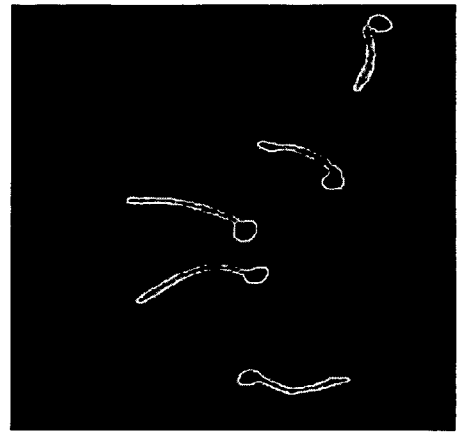
Figure 2C:
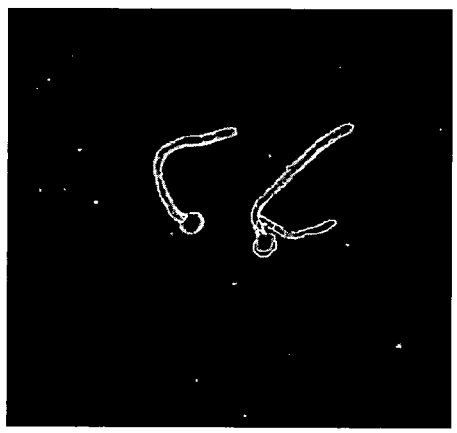
Figure 2D:
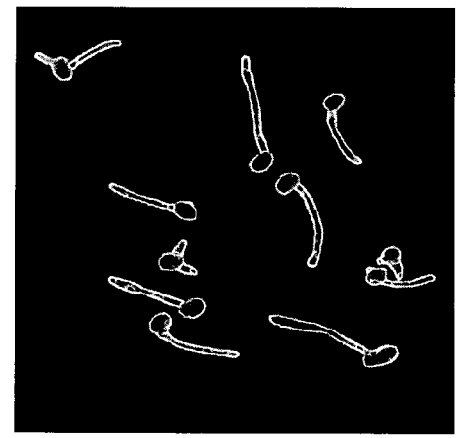

For Als1p to function as an adhesin, it must be located on the cell surface. The cell surface localization of Als1p was verified using indirect immunofluorescence with the anti-Als1p monoclonal antibody. Diffuse staining was detected on the surface of blastospores during exponential growth. This staining was undetectable on blastospores in the stationary phase. Referring to FIG. 2A, when blastospores were induced to produce filaments, intense staining was observed that localized exclusively to the base of the emerging filament. No immunofluorescence was observed with the als1/als1 mutant, confirming the specificity of this antibody for Als1p. See FIG. 2B. These results establish that Als1p is a cell surface protein.

Figure 3A:
FIG. 3A, 3B show the mediation of Als1p on *C. albicans* filamentation on solid medium. *C. albicans* blastospores were spotted on Lee's agar plates and incubated at 37° C. for 4 days (A) or 3 days (B).
Figure 3A:
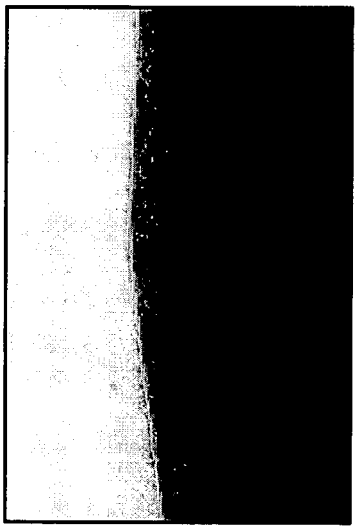
Figure 3A:
Figure 3B:
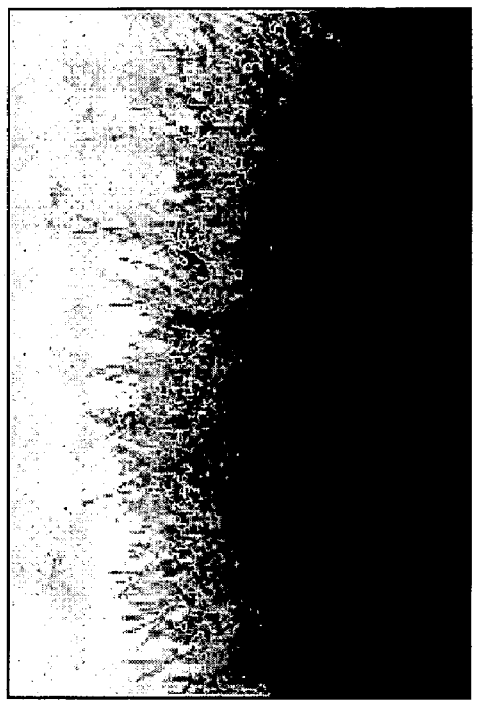
Figure 3B:
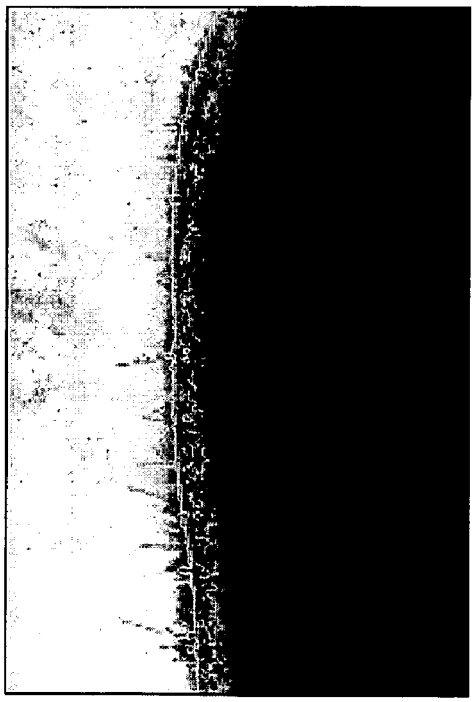
Figure 4A:
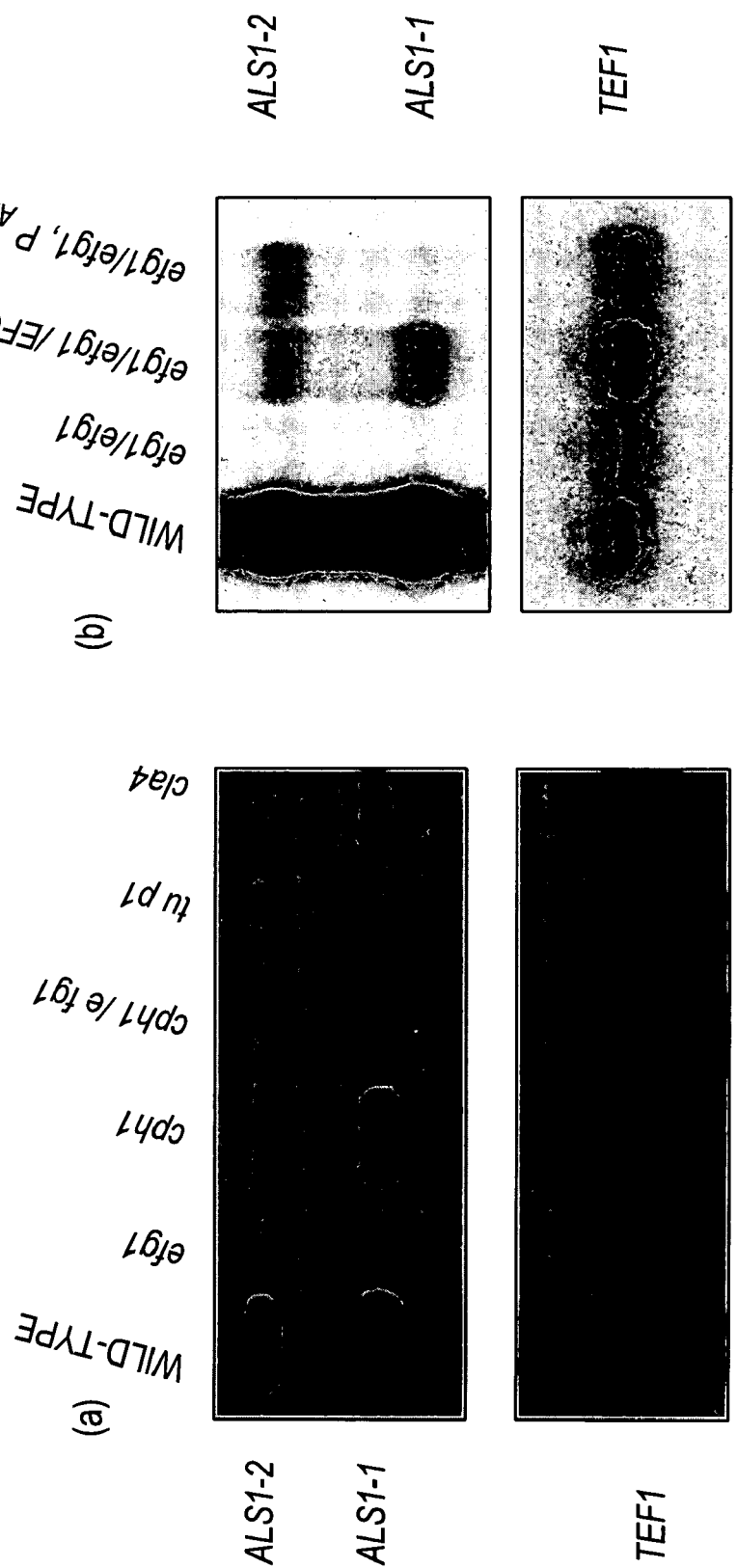
FIG. 4A, 4B show the control of ALS1 expression and the mediation of *C. albicans* filamentation by the EFG1 filamentation regulatory pathway. (A) Northern blot analysis showing expression of ALS1 in (i) mutants deficient in different filamentation regulatory pathways. (ii) efg1/efg1 mutant complemented with either EFG1 or $P_{ADH1}$-ALS1. Total RNA was extracted from cells grown in RPM1 1640+ glutamine medium at 37° C. for 90 minutes to induce filamentation. Blots were probed with ALS1 and TEF1. (B) Photomicrographs of the efg1/efg1 mutant and efg1/efg1 mutant complemented with $P_{ADH1}$-ALS1 grown on Lee's agar plates at 37° C. for 4 days.
Figure 4B:
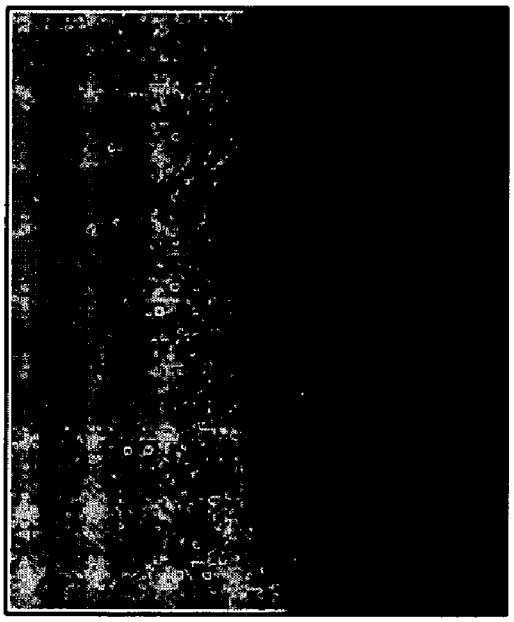
Figure 4B:
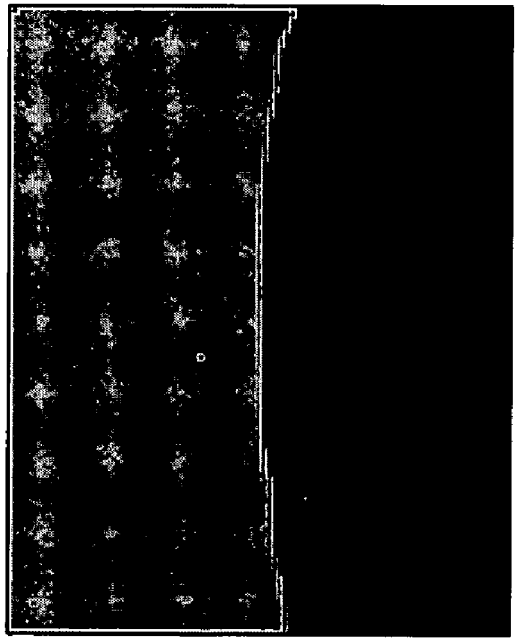

The specific localization of Als1p to the blastospore-filament junction implicates Als1p in the filamentation process. To determine the mechanism, the filamentation phenotype of the *C. albicans* ALS1 mutants was analyzed. Referring to FIG. 3A, the als1/als1 mutant failed to form filaments after a 4 day incubation on Lee's solid medium, while both the ALS1/ALS1 AND ALS1/als1 strains as well as the ALS1-complemented mutant produced abundant filaments at this time point. The als1/als1 mutant was capable of forming filaments after longer periods of incubation. Furthermore, overexpressing ALS1 augmented filamentation: the $P_{ADH1}$-ALS1 strain formed profuse filaments after a 3 day incubation, whereas the wild-type strain produced scant filaments at this time point. See FIG. 3B. To further confirm the role of Als1p in filamentation, a negative control was provided using mutant similar to the ALS1 overexpression mutant, except the coding sequence of the ALS1 was inserted in the opposite orientation. The filamentation phenotype of the resulting strain was shown to be similar to that of the wild-type strain. The filament-inducing properties of Als1p are specific to cells grown on solid media, because all of the strains described above filamented comparably in liquid media. The data demonstrates that Als1p promotes filamentation and implicates ALS1 expression in the regulation of filamentation control pathways. Northern blot analysis of ALS1 expression in mutants with defects in each of these pathways, including efg1/efg1, cph1/cph1, efg1/efg cph1/cph1, tup1/tup1, and cla4/cla4 mutants were performed. Referring to FIG. 4A, mutants in which both alleles of EFG1 had been disrupted failed to express ALS1. Introduction of a copy of wild-type EFG1 into the efg1/efg1 mutant restored ALS1 expression, though at a reduced level. See FIG. 4B. Also, as seen in FIG. 4A, none of the other filamentation regulatory mutations significantly altered ALS1 expression (FIG. 4A). Thus, Efg1p is required for ALS1 expression.

If Efg1p stimulates the expression of ALS1, which in turn induces filamentation, the expression of ALS1 in the efg1/efg1 strain should restore filamentation. A functional allele of ALS1 under the control of the ADH1 promoter was integrated into the efg1/efg1 strain. To investigate the possibility that ALS1 gene product might complement the filamentation defect in efg1 null mutant, an Ura efg1 null mutant was transformed with linearized pAU-1. Ura$^+$ clones were selected and integration of the third copy of ALS1 was confirmed with PCR using the primers: 5'-CCGTTTATAC-CATCCAAATC-3' (SEQ ID NO.5) and 5'-CTACATCCTC-CAATGATATAAC-3' (SEQ ID NO.6). The resulting strain expressed ALS1 autonomously and regained the ability to filament on Lee's agar. See FIGS. 4B and C. Therefore, Efg1p induces filamentation through activation of ALS1 expression.

Because filamentation is a critical virulence factor in *C. albicans*, delineation of a pathway that regulates filamentation has important implications for pathogenicity. Prior to ALS1, no gene encoding a downstream effector of these regulatory pathways had been identified. Disruption of two other genes encoding cell surface proteins, HWP1 AND INT1, results in mutants with filamentation defects. Although HWP1 expression is also regulated by Efg1p, the autonomous expression of HWP1 in the efg1/efg1 mutant fails to restore filamentation. Therefore Hwp1p alone does not function as an effector of filamentation downstream of EFG1. Also, the regulatory elements controlling INT1 expression are not know. Thus, Als1p is the first cell-surface protein identified that functions as a downstream effector of filamentation, thereby suggesting a pivotal role for this protein in the virulence of *C. albicans*.

Figure 5A:
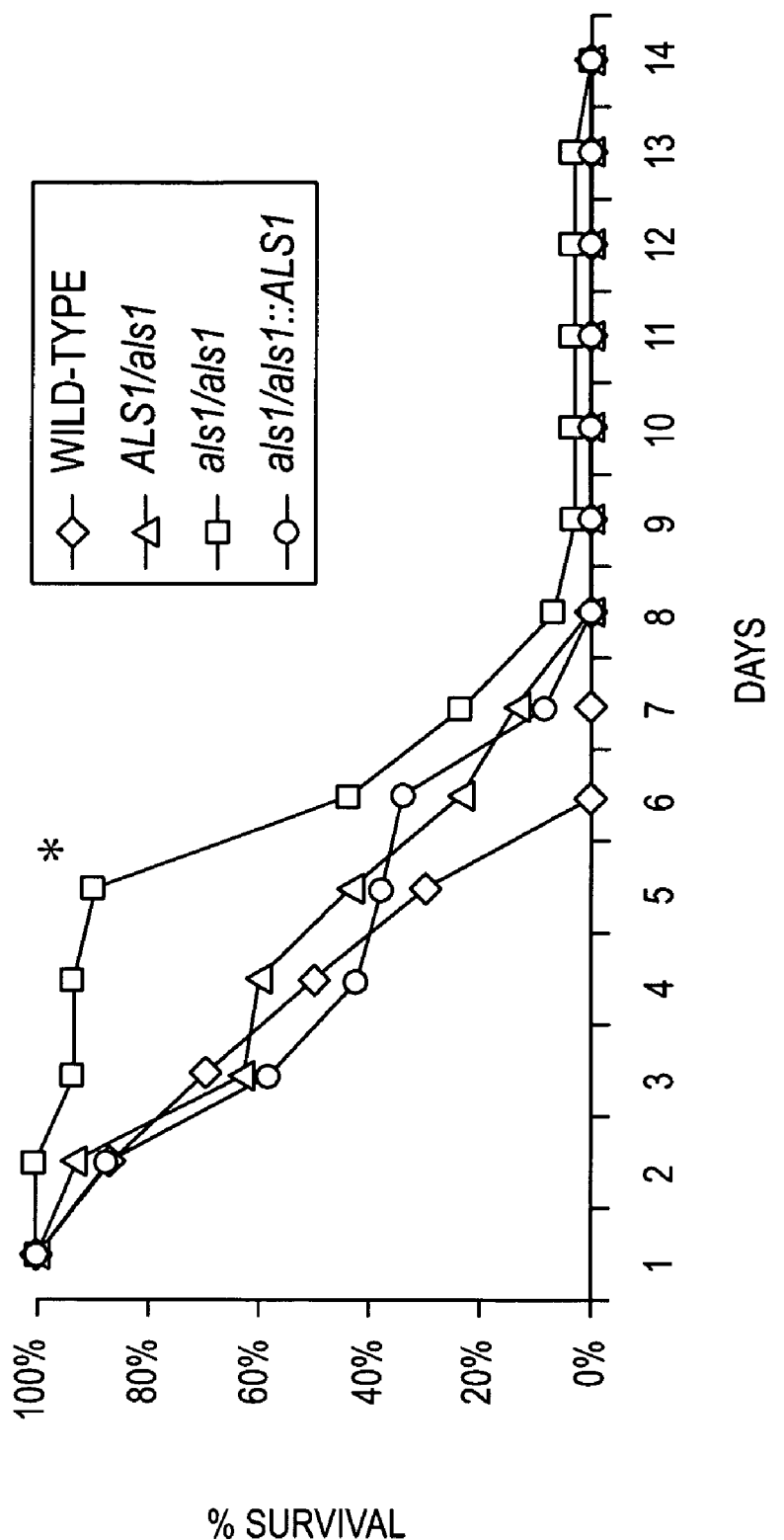
FIG. 5A, 5B show the reduction of virulence in the mouse model of hematogenously disseminated candidiasis by (A) Male Balb/C mice (n=30 for each yeast strain) were injected with stationary phase blastospores ($10^6$ per mouse in 0.5 ml of PBS). Curves are the compiled results of three replicate experiments (n=30 mice for each strain). The doubling times of all strains, grown in YPD at 30° C., ranged between 1.29 to 1.52 hours and were not statistically different from each other. Southern blot analysis of total chromosomal DNA was used to match the identity of the genotype of *C. albicans* strains retrieved from infected organs with those of *C. albicans* strains used to infect the mice. Statistical analysis was obtained by Wilcoxon rank sum test and corrected for multiple comparisons with the Bonferroni correction. *P<0.002 for the als1/als1 mutant versus each of the other strains. (B) Histological micrographs of kidneys infected with *C. albicans* wild-type, homozygous als1 null mutant, or heterozygous ALS1 complemented mutant. Kidney samples were retrieved 28 hours (a) or 40 (b) hours post infection, fixed in paraformaldehyde and sections were stained with silver (magnification, X400). Arrows denote *C. albicans* cells.
Figure 5B:
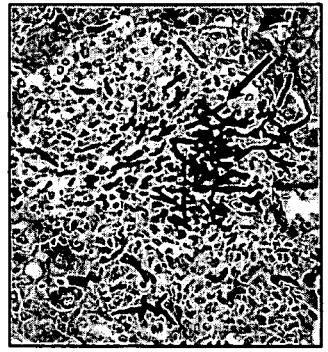
Figure 5B:
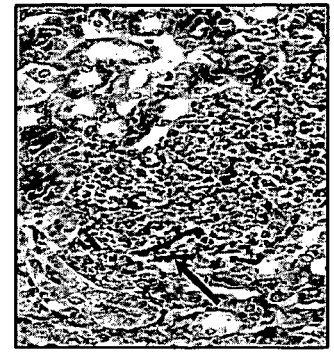
Figure 5B:
Figure 5B:
Figure 5B:
Figure 5B:
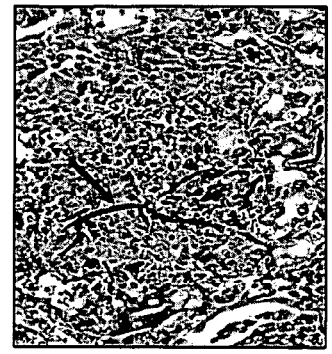

The contribution of Als1p to *C. albicans* virulence was tested in a model of hematogenously disseminated candidiasis, A. S. Ibrahim et al., *Infect. Immun.* 63, 1993 (1995). Referring to FIG. 5A, mice infected with the als1/als1 null mutant survived significantly longer than mice infected with the ALS1/ALS1 strain, the ALS1/als1 mutant or the ALS1-complemented mutant. After 28 hours of infection, the kidneys of mice infected with the als1/als1 mutant contained significantly fewer organisms (5.70±0.46 $\log_{10}$ CFU/g) (P<0.0006 for both comparisons). No difference was detected in colony counts of organisms recovered from spleen, lungs, or liver of mice infected with either of the strains at any of the tested time points. These results indicate that Als1p is important for *C. albicans* growth and persistence in the kidney during the first 28 hours of infection. Referring to FIG. 5B, examination of the kidneys of mice after 28 hours of infection revealed that the als1/als1 mutant produced significantly shorter filaments and elicited a weaker inflammatory response than did either the wild-type of ALS1-complemented strains. However, by 40 hours of infection, the length of the filaments and the number of leukocytes surrounding them were similar for all three strains.

The filamentation defect of the als1/als1 mutant seen on histopathology paralleled the in vitro filamentation assays on solid media. This mutant showed defective filamentation at early time points both in vivo and in vitro. This defect eventually resolved with prolonged infection/incubation. These results suggest that a filamentation regulatory pathway that is independent of ALS1 may become operative at later time points. The activation of this alternative filamentation pathway by 40 hours of infection is likely the reason why mice infected with the als1/als1 mutant subsequently succumbed in the ensuing 2–3 days.

Collectively, these data demonstrate that *C. albicans* ALS1 encodes a cell surface protein that mediates both adherence to endothelial cells and filamentation. Als1p is the only identified downstream effector of any known filamentation regulatory pathway in *C. albicans*. Additionally, Als1p contributes to virulence in hematogenous candidal infection. The cell surface location and dual functionality of Als1p make it an attractive target for both drug and immune-based therapies.

EXAMPLE 3

Purification of ALS1 Adhesin Protein

The ALS1 protein synthesized by *E. coli* is adequate as an immunogen. However, eukaryotic proteins synthesized by *E. coli* may not be functional due to improper folding or lack of glycosylation. Therefore, to determine if the ALS1 protein can block the adherence of *C. albicans* to endothelial cells, the protein is, preferably, purified from genetically engineered *C. albicans*.

PCR was used to amplify a fragment of ALS1, from nucleotides 52 to 1296. This 1246 bp fragment encompassed the N-terminus of the predicted ALS1 protein from the end of the signal peptide to the beginning of the tandem repeats. This region of ALS1 was amplified because it likely encodes the binding site of the adhesin, based on its homology to the binding region of the *S. cerevisiae* Agα1 gene product. In addition, this portion of the predicted ALS1 protein has few glycosylation sites and its size is appropriate for efficient expression in *E. coli*.

The fragment of ALS1 was ligated into pQE32 to produce pINS5. In this plasmid, the protein is expressed under control of the lac promoter and it has a 6-hits tag fused to its N-terminus so that it can be affinity purified. We transformed *E. coli* with pINS5, grew it under inducing conditions (in the presence of IPTG), and then lysed the cells. The cell lysate was passed through a $Ni^{2+}$-agarose column to affinity purify the ALS1-6His fusion protein. This procedure yielded substantial amounts of ALS1-6His. The fusion protein was further purified by SDS-PAGE. The band containing the protein was excised from the gel so that polyclonal rabbit antiserum can be raised against it. It will be appreciated by one skilled in the art that the surface adhesin protein according to the invention may be prepared and purified by a variety of known processes without departing from the spirit of the present invention. The underlying polynucleotide sequence and the polypeptide sequence of Als1p are listed in FIG. 7 (SEQ ID NOS.7 and 8).

EXAMPLE 4

Raising Polyclonal Antisera against ALS1 Protein

To determine whether antibodies against the ALS1 protein block the adherence of Candida albicans to endothelial and epithelial cells, and the selected host constituent in vitro, rabbits were inoculated with S. cerevisiae transformed with ALS1 protein. The immunization protocol used was the dose and schedule used by Hasenclever and Mitchell for production of antisera that identified the antigenic relationship among various species of Candida. Hasenclever, H. F. and W. O. Mitchell. 1960. Antigenic relationships of Torulopsis glabrata and seven species of the genus Candida. J. Bacteriol. 79:677–681. Control antisera were also raised against S. cerevisiae transformed with the empty plasmid. All yeast cells were be grown in galactose to induce expression of the ALS genes. Before being tested in the adherence experiments, the serum was heat-inactivated at 56 C to remove all complement activity.

Sera from immunized rabbits were absorbed with whole cells of S. cerevisiae transformed with empty plasmid to remove antibodies that are reactive with components of the yeast other than ALS1 protein. The titer of the antisera was determined by immunofluorescence using S. cerevisiae that express the ALS1 gene. FITC-labeled anti-rabbit antibodies were purchased from commercial sources (Southern Biotechnology, Inc). Affinity-purified secondary antibodies were essential because many commercially available sera contain antibodies reactive with yeast glucan and mannan. The secondary antibodies were pretested using Candida albicans as well as S. cerevisiae transformed with the plasmid and were absorbed as needed to remove any anti-S. cerevisiae or anti-Candida antibodies. Negative controls were 1) preimmune serum, 2) S. cerevisiae transformed with the empty plasmid, and 3) S. cerevisiae transformed with the ALS gene but grown under conditions that suppress expression of the ALS gene (glucose).

In addition to the above experiments, Western blotting was used to provide further confirmation that an antiserum binds specifically to the ALS protein against which it was raised. S. cerevisiae transformed with the ALS1 were grown under inducing conditions and their plasma membranes were isolated by standard methods. Panaretou, B. and P. Piper. 1996. Isolation of yeast plasma membranes. p. 117–121. In I. H. Evans. (ed.), Yeast Protocols. Methods in Cell and Molecular Biology. Humana Press, Totowa, N.J. Plasma membranes were also prepared from S, cerevisiae transformed with the empty plasmid and grown under identical conditions. The membrane proteins were separated by SDS-PAGE and then transferred to PVDF membrane by electroblotting. Harlow, E. and D. Lane. 1988. Antibodies: a laboratory manual. Cold Spring Harbor Laboratory Press. After being blocked with nonfat milk, the blot was incubated with the ALS antiserum. The preabsorbed antiserum did not react with proteins extracted from S. cerevisiae containing empty plasmid. This antiserum blocked the adherence of S. cerevisiae pYF5 (a clone that expresses Candida albicans ALS1) to endothelial cells.

EXAMPLE 5

Polyclonal Antibodies Against Specific ALS Proteins Prophylactically Protect Mice from Mucosal and Hematogenously Disseminated Candidal Infections Having identified the antisera that block the adherence of a clone of S. cerevisiae transformed with an ALS1 ALS gene under the above conditions, these antisera were demonstrated to protect mice from intravenous challenge with Candida albicans.

The antisera against the ALS proteins were first tested in the murine model of hematogenously disseminated candidiasis. Affinity-purified anti-ALS antibodies are effective in preventing adhesion of yeast cells to various substrates (see EXAMPLE 3). Affinity-purification is useful in this system because antibody doses can be accurately determined. Moreover, the unfractionated antisera will undoubtedly contain large amounts of antibody directed toward antigens on the S. cerevisiae carrier cells. Many of these anti-Saccharomyces antibodies would likely bind to C. albicans and make interpretation of the results impossible. Additionally, it is quite possible that the procedure used to elute antibodies from S. cerevisiae that express the ALS protein may also elute small amounts of yeast mannan or glucan that could have adjuvant-like activity. The immunoaffinity-purified antibodies are further purified before use. They may also be preabsorbed with mouse splenocytes.

Figure 6:
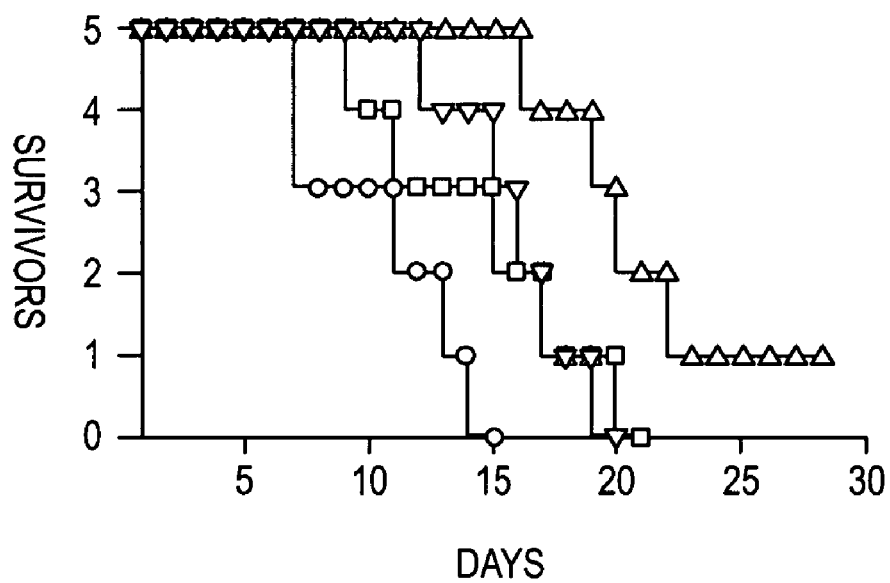
FIG. 6 shows the prophylactic effect of anti-ALS antibody against disseminated candidiasis as a function of surviving animals over a 30-day period for animals infused with anti-Als1p polyserum.

Antibody doses may be administered to cover the range that brackets the levels of serum antibody that can be expected in most active immunization protocols and to cover the range of antibody doses that are typically used for passive immunization in murine models of candidiasis. See Dromer, F., J. Charreire, A. Contrepois, C. Carbon, and P. Yeni. 1987, Protection, of mice against experimental cryptococcosis by anti-Cryptococcus neofornwns monoclonal antibody, Infect. Inimun. 55:749–752; Han, Y. and J. E. Cutler. 1995, Antibody response that protects against disseminated candidiasis, Infect. Immun. 63:2714–2719; Mukherjee, J., M. D. Scharff, and A. Casadevall. 1992, Protective murine monoclonal antibodies to Cryptococcus neofornwns, Infect. Immun. 60:4534–4541; Sanford, J. E., D. M. Lupan, A. M. Schlageter, and T. R. Kozel. 1990, Passive immunization against Cryptococcus neoformans with an isotype-switch family of monoclonal antibodies reactive with cryptococcal polysaccharide, Infect. Inunun. 58:1919–1923. BALB/c mice (female, 7 week old, the NCI) were given anti-ALS that had been absorbed with mouse splenic cells by an intraperitoneal (i.p.) injection. Control mice received prebled serum that had been absorbed with mouse spenic cells, intact anti-ALS serum, or DPBS, respectively. For the pre-absorption, 2 ml of anti-ALS or prebled sera were mixed with 100 µl of mouse (BALB/c, 7 weeks old female, NCI) splenic cells (app. 9×10$^6$ cells per ml) at room temperature for 20 minutes. The mixture was washed with warm sterile DPBS by centrifugation (@ 300× g) for 3 minutes. This procedure was repeated three times. The volume of i.p. injection was 0.4 ml per mouse. Four hours later, the mice were challenged with C. albicans (strain CA-1; 5×10$^5$ hydrophilic yeast cells per mouse) by i.v. injection. Then, their survival times were measured. See FIG. 6.

Previous studies have shown that antibodies administered via the intraperitoneal route are rapidly (within minutes) and almost completely transferred to the serum (Kozel and Casadevall, unpublished observations). As a control for effects of administering the antibody preparations, a parallel group of mice were treated with antibodies isolated from pre-immune serum that has been absorbed with *S. cerevisiae* transformed with the ALS gene. The survival time and numbers of yeast per gram of kidney were measured. Again, referring to FIG. 6, mice infected intravenously with $10^6$ blastopores of ALS1 null mutant had a longer median survival time when compared to mice infected with *Candida albicans* CAI-12 or *Candida albicans* in which one allele of the ALS1 had been deleted (p=0.003).

These results that immunotherapeutic strategies using the ALS1 proteins as a vaccine have a protective prophylactic effect against disseminated candidiasis.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

We claim:

1. A pharmaceutical composition comprising a biocompatible carrier for injection or infusion and an isolated and purified N-terminal fragment of agglutinin-like sequence (ALS1) cell surface adhesin protein of *Candida albicans*, wherein the N-terminal fragment is encoded by a nucleotide sequence consisting of nucleotides 52 to 1296 of SEQ ID NO: 7 and wherein the composition produces antibodies that bind specifically to said ALS1 cell surface adhesin protein.

2. The composition of claim 1, wherein the N-terminal fragment contains the binding site of the ALS1 cell surface adhesin protein.

3. A pharmaceutical composition consisting essentially of a biocompatible carrier for injection or infusion and an isolated and purified N-terminal fragment of agglutinin-like sequence (ALS1) cell surface adhesin protein of *Candida albicans*, wherein the N-terminal fragment is encoded by a nucleotide sequence consisting of nucleotides 52 to 1296 of SEQ ID NO: 7 and wherein the composition produces antibodies that bind specifically to said ALS1 cell surface adhesin protein.

4. The composition of claim 3, wherein the N-terminal fragment contains the binding site of the ALS1 cell surface adhesin protein.

* * * * *

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial sequence
<220> FEATURE:
<223> OTHER INFORMATION: PCR Primer

<400> SEQUENCE: 1
ccgctcgaga tgcttcaaca atttacattg tta                              33

<210> SEQ ID NO 2
<211> LENGTH: 32
<212> TYPE: DNA
<213> ORGANISM: Artificial sequence
<220> FEATURE:
<223> OTHER INFORMATION: PCR Primer

<400> SEQUENCE: 2
ccgctcgagt cactaaatga acaaggacaa ta                               32

<210> SEQ ID NO 3
<211> LENGTH: 31
<212> TYPE: DNA
<213> ORGANISM: Artificial sequence
<220> FEATURE:
<223> OTHER INFORMATION: PCR Primer

<400> SEQUENCE: 3
cgggatccag atgcttcaac aatttacatt g                                31

<210> SEQ ID NO 4
<211> LENGTH: 31
<212> TYPE: DNA
<213> ORGANISM: Artificial sequence
<220> FEATURE:
<223> OTHER INFORMATION: PCR Primer

<400> SEQUENCE: 4
cgggatcctc actaaatgaa caaggacaat a                                31

<210> SEQ ID NO 5
<211> LENGTH: 20
<212> TYPE: DNA
<213> ORGANISM: Artificial sequence
<220> FEATURE:
<223> OTHER INFORMATION: PCR Primer

<400> SEQUENCE: 5
ccgtttatac catccaaatc                                             20
```

<210> SEQ ID NO 6
<211> LENGTH: 22
<212> TYPE: DNA
<213> ORGANISM: Artificial sequence
<220> FEATURE:
<223> OTHER INFORMATION: PCR Primer

<400> SEQUENCE: 6

```
ctacatcctc caatgatata ac                                              22
```

<210> SEQ ID NO 7
<211> LENGTH: 3786
<212> TYPE: DNA
<213> ORGANISM: Candida albicans

<400> SEQUENCE: 7

```
atgcttcaac aatttacatt gttattccta tatttgtcaa ttgcaagtgc aaagacaatc      60
actggtgttt ttgatagttt taattcatta acttggtcca atgctgctaa ttatgctttc     120
aaagggccag gatacccaac ttggaatgct gttttgggtt ggtccttaga tggtaccagt     180
gccaatccag gggatacatt cacattgaat atgccatgtg tgtttaaata tactacttca     240
caaacatctg ttgatttaac tgccgatggt gttaaatatg ctacttgtca attttattct     300
ggtgaagaat tcacaacttt ttctacatta acatgtactg tgaacgacgc tttgaaatca     360
tccattaagg catttggtac agttactttta ccaattgcat tcaatgttgg tggaacaggt    420
tcatcaactg atttggaaga ttctaaatgt tttactgctg gtaccaatac agtcacattt     480
aatgatggtg ataaagatat ctcaattgat gttgagtttg aaaagtcaac cgttgatcca     540
agtgcatatt tgtatgcttc cagagttatg ccaagtctca ataaggtcac aactctttt     600 gtggcaccac aatgtgaaaa tggttacaca tctggtacaa tggggttctc cagtagtaac     660
ggtgacgttg ctattgattg ctcaaatatt catattggta tcacaaaagg attaaatgat     720
tggaattatc cggtttcatc tgaatcattt agttacacta aaacttgtac atctaatgga     780
attcagatta aatatcaaaa tgtacctgct ggttatcgtc catttattga tgcttatatt     840
tctgctacag atgttaacca atatacttta gcatatacca atgattatac ttgtgctggc     900
agtcgtctgc aaagtaaacc tttcactttta agatggactg gatacaagaa tagtgatgcc     960
ggatctaacg gtattgtcat tgttgctaca actagaacag ttacagacag taccactgct    1020
gtcactactt taccattcaa tccaagtgtt gataaaacca aaacaatcga aattttgcaa    1080
cctattccaa ccactaccat cacaacttca tatgttggtg tgactacttc ctatctgact    1140
aagactgcac caattggtga aacagctact gttattgttg atgtgccata tcatactacc    1200
acaactgtta ccagtgaatg gacaggaaca atcactacca ccacaactcg taccaatcca    1260
actgattcaa ttgacacagt ggtggtacaa gttccactgc caaatccaac tgttagtact    1320
actgaatatt ggtctcagtc ctttgctaca accactacag ttactgctcc tccaggtggt    1380
accgatactg tgattatcag agagccacca aaccatactg tcactactac tgaatattgg    1440
tcacaatcct ttgctactac tactactgtt actgctcctc caggtggtac tgactcagta    1500
attatcagag aaccaccaaa tccaactgtc actacaaccg agtattggtc tcaatccttt    1560
gctactacta ctacagttac tgctcctcca ggtggtactg actcagtaat tatcagagaa    1620
cctccaaacc caactgtcac caccactgaa tattggtccc aatcttacgc aaccacaact    1680
actgtgactg ctcctccagg aggcactgac tcagtaatta tcagagaacc accaaaccac    1740
actgtcacta ctactgaata ctggtcacaa tcatatgcca ccactaccac tgtaactgca    1800
```

```
ccaccaggtg gtactgacac tgttatcatt agagagccac caaaccacac tgtcactact    1860
actgagtatt ggtctcaatc gtttgctact accacaactg taactggtcc accaagtggc    1920
actgatactg ttatcattag ggaaccacca aacccaactg tcaccactac tgaatactgg    1980
tctcaatcat atgcaaccac tactaccatt accgctccac ctggtgaaac tgataccgtt    2040
cttatcagag agccaccaaa ccatactgtc actactactg aatactggtc tcaatcatat    2100
gctacaacca ccactgttac tgcaccacct ggtgaaaccg ataccgttct tatcagagag    2160
ccaccaaacc atactgtcac tactactgaa tactggtctc aatcatatgc tacaaccacc    2220
actgttactg caccaccagg tggtaccgat actgttatca ttagagagcc accaaatcca    2280
acagttacta ctactgaata ttggtcacaa tcatttgcca caaccaccac agttactgct    2340
cctccaggtg gtactgacac tgtgattatc tatgaaagca tgtcaagttc aaagatttct    2400
acatcctcca atgatataac cagtatcatt ccatcatttt cccgtcctca ttatgtcaac    2460
agcacaacct ccgatttgtc aacatttgaa tcttcatcca tgaatactcc tacttctatc    2520
agtagtgatg gtatgttgtt gtcttctaca actttggtta ctgaatcaga acaactaca    2580 gaactgattt gcagtgatgg taaagagtgt tctagattgt ccagttcttc tggtattgtc    2640
acaaatccag atagcaatga atcctcaatc gtaactagta ctgttcctac tgcaagtaca    2700
atgtctgatt cactttcttc aactgatggt attagtgcta catcttctga taatgtttca    2760
aaatcaggag tatcagttac aaccgaaact tctgttacaa ctattcaaac tactccaaac    2820
ccattatcat cttcagtgac atcattgact cagttgtctt caattccaag tgtttcagaa    2880
agtgaaagta agttacatt tacaagcaat ggagacaacc aaagtggtac tcatgattca    2940
caatctactt ccactgaaat tgaaattgta acaaccagtt ctactaaagt tttaccacct    3000
gtcgtttctt ctaatactga tttgactagt gaaccaacaa ataccagaga caaccaact    3060 acattatcaa ctacttcaaa ctccatcact gaagatatca ccacatctca acctacaggt    3120
gataatggag acaatacttc atcaaccaat ccagttccaa ctgtggcaac aagtactta    3180 gcatctgcaa gtgaagaaga caacaaaagc ggttctcatg aatcagcatc cacaagtttg    3240
aaaccaagta tgggtgaaaa ttctggatta actacttcta ctgaaattga agctacaaca    3300
accagtccta cagaagctcc atcacctgct gtttcttctg gtactgatgt aactactgaa    3360
ccaactgata ctagagaaca acctactaca ttatcaacta cttcaaaaac aaacagtgaa    3420
ctggttgcta ctacacaagc tactaatgaa aatggtggta atctccatc aactgattta    3480 acatcaagct tgacaacagg caccctcagca tctacaagtg ctaatagcga acttgttact    3540
agtggatctg ttactggtgg agctgttgcc agtgcttcaa atgatcaatc acattctact    3600
tctgttacca acagcaacag cattgtatct aatacccac aaactacatt gagtcaacaa    3660
gttacctcat cctcacctc aaccaacaca ttcattgctt ctacatacga tggctctggt    3720
tctattatcc aacattctac ttggttgtac ggtttgatca cattattgtc cttgttcatt    3780
tagtga                                                              3786

<210> SEQ ID NO 8
<211> LENGTH: 1260
<212> TYPE: PRT
<213> ORGANISM: Candida albicans

<400> SEQUENCE: 8

Met Leu Gln Gln Phe Thr Leu Leu Phe Leu Tyr Leu Ser Ile Ala Ser
1               5                   10                  15
```

-continued

```
Ala Lys Thr Ile Thr Gly Val Phe Asp Ser Phe Asn Ser Leu Thr Trp
            20              25              30

Ser Asn Ala Ala Asn Tyr Ala Phe Lys Gly Pro Gly Tyr Pro Thr Trp
        35              40              45

Asn Ala Val Leu Gly Trp Ser Leu Asp Gly Thr Ser Ala Asn Pro Gly
50              55              60

Asp Thr Phe Thr Leu Asn Met Pro Cys Val Phe Lys Tyr Thr Thr Ser
65              70              75              80

Gln Thr Ser Val Asp Leu Thr Ala Asp Gly Val Lys Tyr Ala Thr Cys
            85              90              95

Gln Phe Tyr Ser Gly Glu Glu Phe Thr Thr Phe Ser Thr Leu Thr Cys
            100             105             110

Thr Val Asn Asp Ala Leu Lys Ser Ile Lys Ala Phe Gly Thr Val
            115             120             125

Thr Leu Pro Ile Ala Phe Asn Val Gly Gly Thr Gly Ser Ser Thr Asp
130             135             140

Leu Glu Asp Ser Lys Cys Phe Thr Ala Gly Thr Asn Thr Val Thr Phe
145             150             155             160

Asn Asp Gly Asp Lys Asp Ile Ser Ile Asp Val Glu Phe Glu Lys Ser
            165             170             175

Thr Val Asp Pro Ser Ala Tyr Leu Tyr Ala Ser Arg Val Met Pro Ser
            180             185             190

Leu Asn Lys Val Thr Thr Leu Phe Val Ala Pro Gln Cys Glu Asn Gly
            195             200             205

Tyr Thr Ser Gly Thr Met Gly Phe Ser Ser Asn Gly Asp Val Ala
            210             215             220

Ile Asp Cys Ser Asn Ile His Ile Gly Ile Thr Lys Gly Leu Asn Asp
225             230             235             240

Trp Asn Tyr Pro Val Ser Ser Glu Ser Phe Ser Tyr Thr Lys Thr Cys
            245             250             255

Thr Ser Asn Gly Ile Gln Ile Lys Tyr Gln Asn Val Pro Ala Gly Tyr
            260             265             270

Arg Pro Phe Ile Asp Ala Tyr Ile Ser Ala Thr Asp Val Asn Gln Tyr
            275             280             285

Thr Leu Ala Tyr Thr Asn Asp Tyr Thr Cys Ala Gly Ser Arg Leu Gln
            290             295             300

Ser Lys Pro Phe Thr Leu Arg Trp Thr Gly Tyr Lys Asn Ser Asp Ala
305             310             315             320

Gly Ser Asn Gly Ile Val Ile Val Ala Thr Thr Arg Thr Val Thr Asp
            325             330             335

Ser Thr Thr Ala Val Thr Thr Leu Pro Phe Asn Pro Ser Val Asp Lys
            340             345             350

Thr Lys Thr Ile Glu Ile Leu Gln Pro Ile Pro Thr Thr Thr Ile Thr
            355             360             365

Thr Ser Tyr Val Gly Val Thr Thr Ser Tyr Leu Thr Lys Thr Ala Pro
            370             375             380

Ile Gly Glu Thr Ala Thr Val Ile Val Asp Val Pro Tyr His Thr Thr
385             390             395             400

Thr Thr Val Thr Ser Glu Trp Thr Gly Thr Ile Thr Thr Thr Thr Thr
            405             410             415

Arg Thr Asn Pro Thr Asp Ser Ile Asp Thr Val Val Gln Val Pro
            420             425             430

Leu Pro Asn Pro Thr Val Ser Thr Thr Glu Tyr Trp Ser Gln Ser Phe
```

```
                435                 440                 445
Ala Thr Thr Thr Thr Val Thr Ala Pro Pro Gly Gly Thr Asp Thr Val
450                 455                 460
Ile Ile Arg Glu Pro Pro Asn His Thr Val Thr Thr Thr Glu Tyr Trp
465                 470                 475                 480
Ser Gln Ser Phe Ala Thr Thr Thr Val Thr Ala Pro Pro Gly Gly
                485                 490                 495
Thr Asp Ser Val Ile Ile Arg Glu Pro Pro Asn Pro Thr Val Thr Thr
                500                 505                 510
Thr Glu Tyr Trp Ser Gln Ser Phe Ala Thr Thr Thr Val Thr Ala
        515                 520                 525
Pro Pro Gly Gly Thr Asp Ser Val Ile Ile Arg Glu Pro Pro Asn Pro
530                 535                 540
Thr Val Thr Thr Thr Glu Tyr Trp Ser Gln Ser Tyr Ala Thr Thr Thr
545                 550                 555                 560
Thr Val Thr Ala Pro Pro Gly Gly Thr Asp Ser Val Ile Ile Arg Glu
                565                 570                 575
Pro Pro Asn His Thr Val Thr Thr Thr Glu Tyr Trp Ser Gln Ser Tyr
                580                 585                 590
Ala Thr Thr Thr Val Thr Ala Pro Pro Gly Gly Thr Asp Thr Val
        595                 600                 605
Ile Ile Arg Glu Pro Pro Asn His Thr Val Thr Thr Thr Glu Tyr Trp
        610                 615                 620
Ser Gln Ser Phe Ala Thr Thr Thr Val Thr Gly Pro Pro Ser Gly
625                 630                 635                 640
Thr Asp Thr Val Ile Ile Arg Glu Pro Pro Asn Pro Thr Val Thr Thr
                645                 650                 655
Thr Glu Tyr Trp Ser Gln Ser Tyr Ala Thr Thr Thr Ile Thr Ala
                660                 665                 670
Pro Pro Gly Glu Thr Asp Thr Val Leu Ile Arg Glu Pro Pro Asn His
        675                 680                 685
Thr Val Thr Thr Thr Glu Tyr Trp Ser Gln Ser Tyr Ala Thr Thr Thr
        690                 695                 700
Thr Val Thr Ala Pro Pro Gly Glu Thr Asp Thr Val Leu Ile Arg Glu
705                 710                 715                 720
Pro Pro Asn His Thr Val Thr Thr Thr Glu Tyr Trp Ser Gln Ser Tyr
                725                 730                 735
Ala Thr Thr Thr Thr Val Thr Ala Pro Pro Gly Gly Thr Asp Thr Val
        740                 745                 750
Ile Ile Arg Glu Pro Pro Asn Pro Thr Val Thr Thr Thr Glu Tyr Trp
        755                 760                 765
Ser Gln Ser Phe Ala Thr Thr Thr Val Thr Ala Pro Pro Gly Gly
770                 775                 780
Thr Asp Thr Val Ile Ile Tyr Glu Ser Met Ser Ser Lys Ile Ser
785                 790                 795                 800
Thr Ser Ser Asn Asp Ile Thr Ser Ile Ile Pro Ser Phe Ser Arg Pro
                805                 810                 815
His Tyr Val Asn Ser Thr Thr Ser Asp Leu Ser Thr Phe Glu Ser Ser
                820                 825                 830
Ser Met Asn Thr Pro Thr Ser Ile Ser Ser Asp Gly Met Leu Leu Ser
        835                 840                 845
Ser Thr Thr Leu Val Thr Glu Ser Glu Thr Thr Thr Glu Leu Ile Cys
        850                 855                 860
```

```
Ser Asp Gly Lys Glu Cys Ser Arg Leu Ser Ser Ser Gly Ile Val
865                 870                 875                 880

Thr Asn Pro Asp Ser Asn Glu Ser Ser Ile Val Thr Ser Thr Val Pro
                885                 890                 895

Thr Ala Ser Thr Met Ser Asp Ser Leu Ser Ser Thr Asp Gly Ile Ser
            900                 905                 910

Ala Thr Ser Ser Asp Asn Val Ser Lys Ser Gly Val Ser Val Thr Thr
                915                 920                 925

Glu Thr Ser Val Thr Thr Ile Gln Thr Thr Pro Asn Pro Leu Ser Ser
    930                 935                 940

Ser Val Thr Ser Leu Thr Gln Leu Ser Ser Ile Pro Ser Val Ser Glu
945                 950                 955                 960

Ser Glu Ser Lys Val Thr Phe Thr Ser Asn Gly Asp Asn Gln Ser Gly
                965                 970                 975

Thr His Asp Ser Gln Ser Thr Ser Thr Glu Ile Glu Ile Val Thr Thr
                980                 985                 990

Ser Ser Thr Lys Val Leu Pro Pro Val Val Ser Ser Asn Thr Asp Leu
        995                 1000                1005

Thr Ser Glu Pro Thr Asn Thr Arg Glu Gln Pro Thr Thr Leu Ser
    1010                1015                1020

Thr Thr Ser Asn Ser Ile Thr Glu Asp Ile Thr Thr Ser Gln Pro
    1025                1030                1035

Thr Gly Asp Asn Gly Asp Asn Thr Ser Ser Thr Asn Pro Val Pro
    1040                1045                1050

Thr Val Ala Thr Ser Thr Leu Ala Ser Ala Ser Glu Glu Asp Asn
    1055                1060                1065

Lys Ser Gly Ser His Glu Ser Ala Ser Thr Ser Leu Lys Pro Ser
    1070                1075                1080

Met Gly Glu Asn Ser Gly Leu Thr Thr Ser Thr Glu Ile Glu Ala
    1085                1090                1095

Thr Thr Thr Ser Pro Thr Glu Ala Pro Ser Pro Ala Val Ser Ser
    1100                1105                1110

Gly Thr Asp Val Thr Thr Glu Pro Thr Asp Thr Arg Glu Gln Pro
    1115                1120                1125

Thr Thr Leu Ser Thr Thr Ser Lys Thr Asn Ser Glu Leu Val Ala
    1130                1135                1140

Thr Thr Gln Ala Thr Asn Glu Asn Gly Gly Lys Ser Pro Ser Thr
    1145                1150                1155

Asp Leu Thr Ser Ser Leu Thr Thr Gly Thr Ser Ala Ser Thr Ser
    1160                1165                1170

Ala Asn Ser Glu Leu Val Thr Ser Gly Ser Val Thr Gly Gly Ala
    1175                1180                1185

Val Ala Ser Ala Ser Asn Asp Gln Ser His Ser Thr Ser Val Thr
    1190                1195                1200

Asn Ser Asn Ser Ile Val Ser Asn Thr Pro Gln Thr Thr Leu Ser
    1205                1210                1215

Gln Gln Val Thr Ser Ser Ser Pro Ser Thr Asn Thr Phe Ile Ala
    1220                1225                1230

Ser Thr Tyr Asp Gly Ser Gly Ser Ile Ile Gln His Ser Thr Trp
    1235                1240                1245

Leu Tyr Gly Leu Ile Thr Leu Leu Ser Leu Phe Ile
    1250                1255                1260
```